United States Patent [19]
Naito et al.

[11] Patent Number: 5,656,198
[45] Date of Patent: Aug. 12, 1997

[54] TOLAN COMPOUND AND LIQUID CRYSTAL COMPOSITION CONTAINING THE SAME

[75] Inventors: Tomijiro Naito, Asaka; Yumiko Sakamaki, Sayama; Katsuji Niino, Kawanishi; Kikuo Yamamoto, Habikino, all of Japan

[73] Assignee: Citizen Watch Co., Ltd., Tokyo, Japan

[21] Appl. No.: 628,028

[22] Filed: Apr. 4, 1996

[30] Foreign Application Priority Data

| | | | |
|---|---|---|---|
| Apr. 7, 1995 | [JP] | Japan | 7-082686 |
| Aug. 24, 1995 | [JP] | Japan | 7-216027 |
| Aug. 24, 1995 | [JP] | Japan | 7-216028 |
| Dec. 21, 1995 | [JP] | Japan | 7-333430 |
| Dec. 25, 1995 | [JP] | Japan | 7-337119 |

[51] Int. Cl.⁶ .......... C09K 19/52; C09K 19/30; G02F 1/13
[52] U.S. Cl. .......... 252/299.01; 252/299.63; 252/299.66; 252/299.67; 349/182
[58] Field of Search .......... 252/299.01, 299.63, 252/299.66, 299.67; 359/103; 349/182; 428/1

[56] References Cited

PUBLICATIONS

Tinh et al., "Synthesis and Mesomorphic properties of the Homologous Series of 4-Alkyl or Alkory-4'-Bromo or Cyanotolanes", Mol. Cryst. Liq. Cryst., 1980, vol. 62, pp. 125–140.

*Primary Examiner*—Shean C. Wu
*Attorney, Agent, or Firm*—Oblon, Spivak, McClelland, Maier & Neustadt, P.C.

[57] ABSTRACT

A novel tolan compound of the formula (I):

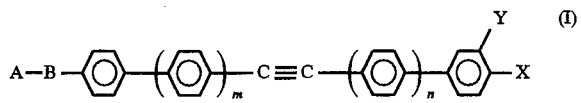

wherein A is a substituted or unsubstituted cyclohexyl or phenyl group; B is —CO—O— or —O—CO—; X is a hydrogen atom, a halogen atom, a cyano group, a $C_1$–$C_{10}$ alkyl group, or a $C_1$–$C_{10}$ alkoxy group; Y is a hydrogen atom or a halogen atom; and m and n are an integer of 0 or 1, provided that m+n=0 or 1. The tolan compound can raise the N-I point and increase the double refractive index ($\Delta n$) of liquid crystal compositions. The liquid crystal composition containing this tolan compound has excellent characteristics as a liquid crystal material, and the liquid crystal display device using this liquid crystal composition has a wide temperature range and a wide visible angle and can be operated at a low driving voltage.

9 Claims, 23 Drawing Sheets

TOLAN COMPOUND AND LIQUID CRYSTAL COMPOSITION CONTAINING THE SAME

BACKGROUND OF THE INVENTION

1. Field of the Invention

The present invention relates to a tolan compound which is useful as a liquid crystal material and to a liquid crystal composition containing this tolan compound.

2. Discussion of the Background

A liquid crystal display device has been widely utilized for a watch, an electronic calculator as well as a word processor, a television set, etc. Of these liquid crystal display devices, particularly frequently used is a liquid crystal display device which utilized optical anisotropy and dielectric anisotropy of a liquid crystal material.

A wide liquid crystal temperature range, a low viscosity to ensure a rapid electro-optical response rate, a suitable double refractive index (Δn) to provide a wide visual scope and a high contrast, a large dielectric anisotropy (Δε) to ensure a low driving voltage, and the characteristics to be chemically and optically stable are given as the characteristics required for a liquid crystal material to be used for liquid crystal display devices.

Liquid crystal compositions presently used are usually prepared by mixing a compound having a liquid crystal phase near room temperatures and a compound having a liquid crystal phase at temperatures higher than room temperatures. In order for a liquid crystal display device to be used outdoor the liquid crystal must be stable in the temperature range of −40° C. to 90° C. In addition, because of the temperature dependency of optical anisotropy and dielectric anisotropy, that is, because of occurrence of sudden change near the N-I point (nematic anisotropy phase transfer temperature), it is necessary to use a liquid crystal material with a high N-I point.

Furthermore, to ensure a wide visual angle and a high contrast the retardation of liquid crystal phase, Δn·d, wherein Δn is the double refractive index of the liquid crystal material and d is the thickness of liquid crystal layer, must be optimized. However, because the thickness of liquid crystal layer (d) is limited to a certain range and a high response rate is required for liquid crystal display devices actually used, the thickness of liquid crystal layer (d) tends to be thin. Because of this reason, a liquid crystal materials with a large double refractive index (Δn) is required.

A driving voltage is dependent on a threshold voltage Vth, whereas the threshold voltage Vth is inversely proportional to the square root of dielectric anisotropy (Δε). Accordingly, the threshold voltage Vth can be kept low when a liquid crystal material with a positive value of dielectric anisotropy (Δε) is used.

Although various liquid crystal compounds have been developed and put on use up to the present time, these is no single liquid crystal compound satisfying all the characteristics mentioned above. Therefore, in practice, several kinds of liquid crystal compounds having different characteristics or non-liquid crystal compounds are mixed and used. Such mixtures, however, are not necessarily satisfactory.

4-Alkyl-4'-alkoxytolan (German Patent No. 2226376) and 4-alkyl-4'-fuluorotolan (Japanese Patent Application Laid-Open No. 260031/1986) are examples of known tolan compounds which are used mixed for the above-mentioned purpose. The mixtures of these tolan compounds, however, are not necessarily satisfactory.

As described above, in spite of various studies in the past on liquid crystal compositions no material which sufficiently satisfies all above characteristics has been found. Each compound used for liquid crystal materials has merits and demerits in its characteristics. In addition, the degree of the above required characteristics is different depending on the liquid crystal display device. The development of a novel liquid crystal compound and a liquid crystal additive which can provide characteristics depending on the intended object of a liquid crystal display device has been desired. Accordingly, an object of the present invention is to provide a novel tolan compound which, if added to a liquid crystal composition, can raise the N-I point and increase the double refractive index (Δn) of the liquid crystal composition. Another object of the present invention is to provide such a liquid crystal composition comprising this novel tolan compound.

SUMMARY OF THE INVENTION

Accordingly, a specific object of the present invention is to provide a tolan compound represented by the following formula (I):

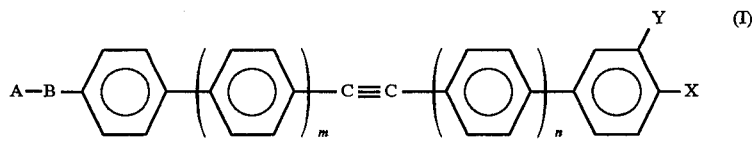

wherein A represents a cyclohexyl group which may be substituted by an alkyl group having 1–10 carbon atoms, or a group represented by the following formula,

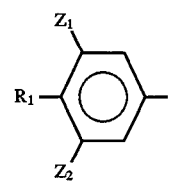

wherein $R_1$ represents a hydrogen atom, a halogen atom, a cyano group, an alkyl group having 1–10 carbon atoms, or an alkoxy group having 1–10 carbon atoms; and $Z_1$ and $Z_2$ represent a hydrogen atom or a halogen atom;

B represents a group,

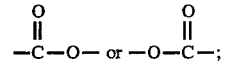

X represents a hydrogen atom, a halogen atom, a cyano group, an alkyl group having 1–10 carbon atoms, or an alkoxy group having 1–10 carbon atoms;

Y represents a hydrogen atom or a halogen atom; and m and n is an integer of 0 or 1, provided that m+n is 0 or 1; provided further that when A is a cyclohexyl group which may be substituted by an alkyl group having 1–10 carbon atoms and m+n is 0, X is a halogen atom, a cyano group, or an alkoxy group having 1–10 carbon atoms.

Another object of the present invention is to provide a liquid crystal composition comprising at least one tolan compound represented by the above formula (I).

A still another object of the present invention is to provide liquid crystal display device using the liquid crystal composition comprising at least one tolan compound represented by the above formula (I).

Other objects, features and advantages of the invention will hereinafter become more readily apparent from the following description.

DETAILED DESCRIPTION OF THE PREFERRED EMBODIMENTS

Figure 1:
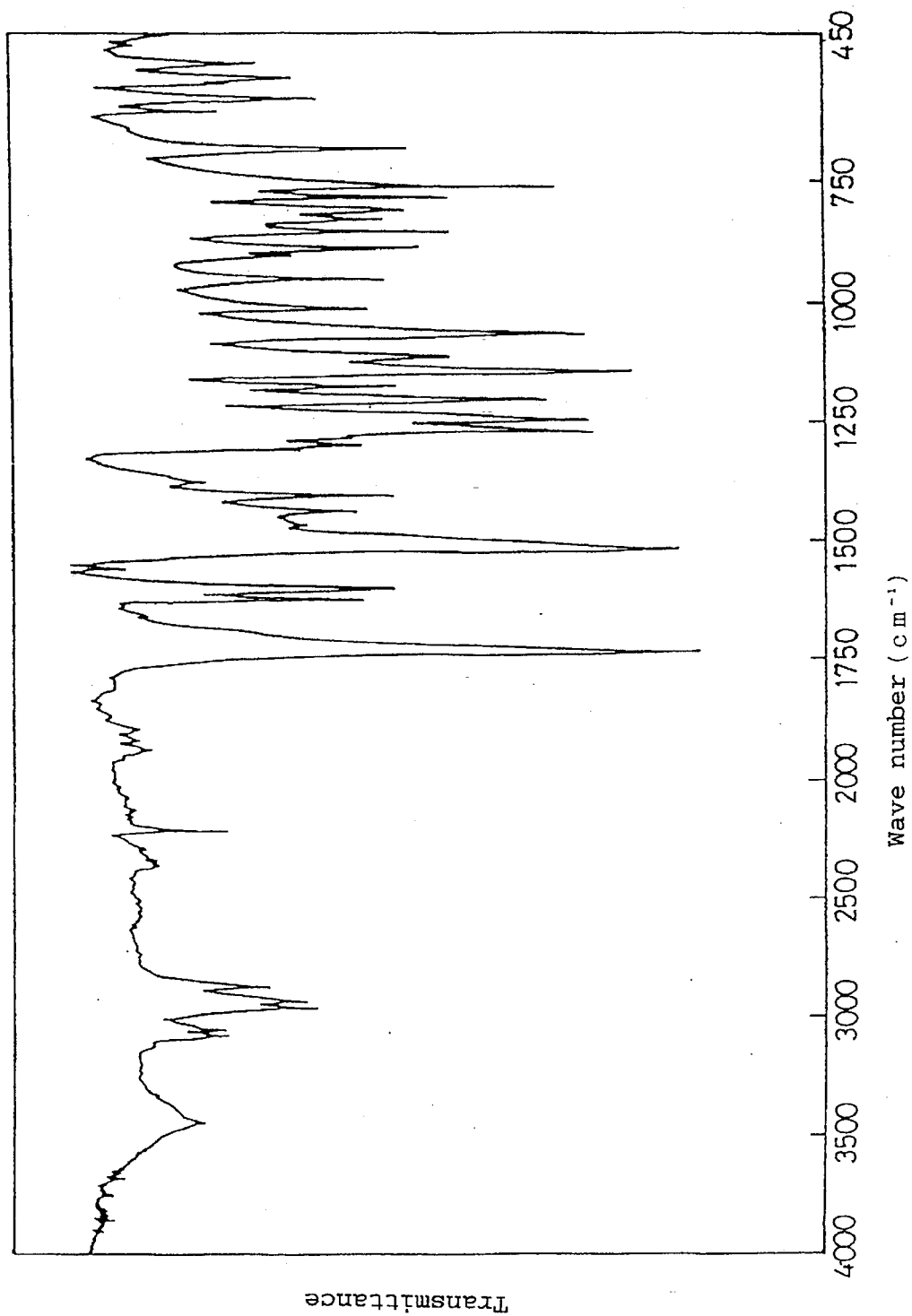
FIG. 1 is a diagram showing an infrared absorption spectrum of the tolan compound prepared in Example 1.

The halogen atom which is present in the tolan compound of the present invention as a substituent is preferably fluorine atom in view of the viscosity and specific resistance of the tolan compound, although chlorine atom and bromine atom are acceptable.

The tolan compound of the present invention may be mixed with various liquid crystal compounds to produce liquid crystal compositions. Esters, cyclohexylphenyl compounds, biphenyl compounds, pyrimidine compounds, dioxane compounds, tolan compounds (other than tolan compounds of the present invention) are given as the liquid crystalline compounds which can be mixed with the tolan compound of the present invention. A mixture of two or more of these liquid crystal compounds may be further mixed with the tolan compound of the present invention.

As mentioned above, the liquid crystal composition comprising the tolan compound of the present invention has excellent characteristics as a liquid crystal material, and the liquid crystal display device using this liquid crystal composition has a wide temperature range and a wide visible angle and can be operated at a low driving voltage.

The amount of the tolan compound of the present invention to be incorporated in the liquid crystal composition varies depending on the types and amounts of other liquid crystalline compounds and cannot be generically determined. Usually, an amount of 1–50% by weight is preferable, with a more preferable amount being 3–20% by weight.

The compound (I) of the present invention can be grouped into the following compounds (Ia) to (Ic).

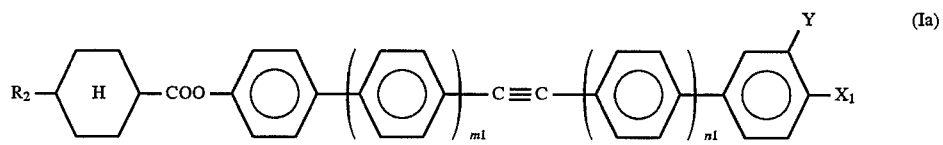

(Ia)

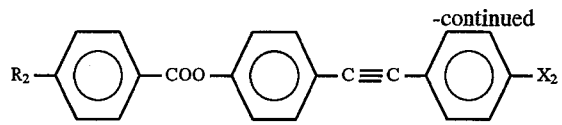

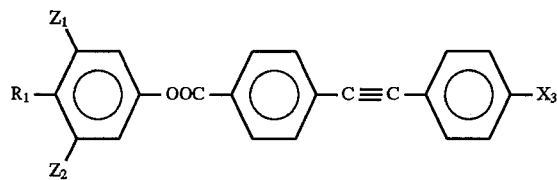

wherein $R_2$ represents a hydrogen atom or an alkyl group having 1–10 carbon atoms; $X_1$ represents a halogen atom, an alkyl group having 1–10 carbon atoms, or an alkoxy group having 1–10 carbon atoms; $X_2$ represents a halogen atom, a cyano group, or an alkoxy group having 1–10 carbon atoms; $X_3$ represents a hydrogen atom or an alkyl group having 1–10 carbon atoms; $Z_1$ and $Z_2$ individually represent a hydrogen atom or a halogen atom; and m1 and n1 is an integer of 0 or 1, provided that m1+n1 is 0 or 1; and $R_1$ has the same meaning as defined above.

The tolan compound (Ia) of the present invention is an excellent compound which, when added to a liquid crystal composition, can increase the N-I point and double refractive index ($\Delta n$) of the liquid crystal composition.

The tolan compound (Ib) of the present invention is an excellent compound which, when added to a liquid crystal composition, can increase the N-I point and double refractive index ($\Delta n$) without significantly changing the viscosity $\eta$ and threshold voltage Vth of the liquid crystal composition.

The tolan compound (Ic) of the present invention is an excellent compound which, when added to a liquid crystal composition, can increase the N-I point and double refractive index ($\Delta n$) of the liquid crystal composition. In addition, the tolan compound (Ic) having a cyano group or a halogen atom for the terminal group $R_1$ has a decreased threshold voltage Vth.

The processes for preparing the tolan compounds of the present invention will now be illustrated.

Process 1:

The compound (Ia) can be prepared by reacting an acid chloride (a) and a substituted phenol (b) in an inert organic solvent such as pyridine; recrystallizing, washing, and drying the reaction product to produce an ester (c); reacting the ester (c) with a phenyl acetylene compound (d) in the presence of triethylamine; and washing with water, drying, and recrystallizing the resulting reaction product according to the following reaction scheme.

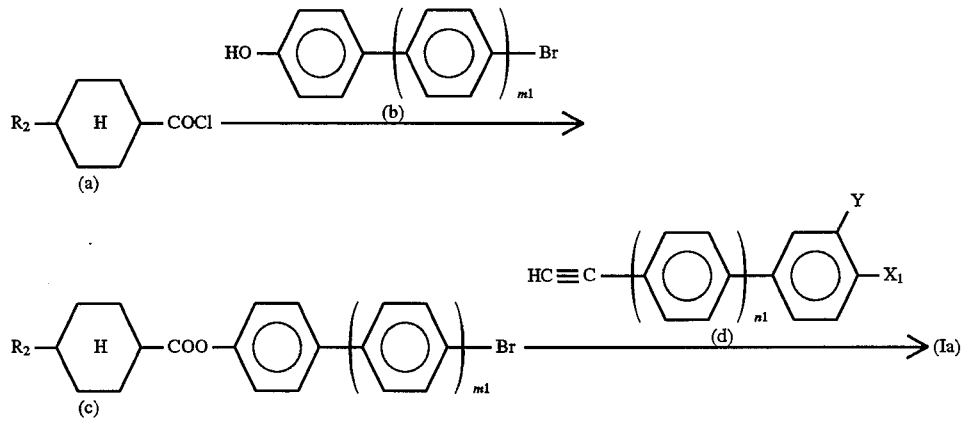

wherein $R_2$, $X_1$, Y, m1 and n1 have the same meaning defined above.

Process 2:

The compound (Ib) can be prepared in the similar manner as in Process 1 according to the following reaction scheme.

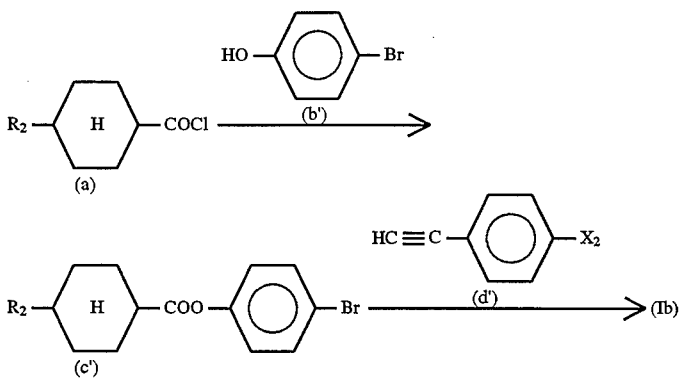

wherein $R_2$ and $X_2$ have the same meaning defined above.

Process 3:

The compound (Ic) can be prepared by reacting bromobenzoic acid (e) and a halogenating agent such as thionyl chloride to obtain an acid chloride (f); reacting the acid chloride (f) with a substituted phenol (g) in an inert organic solvent such as pyridine; recrystallizing, washing with water, and drying the reaction product to produce an ester of the bromobenzoic acid and the substituted phenol (h); reacting the ester (h) with an alkyl phenyl acetylene (i) in the presence of triethylamine; and washing, drying, and recrystallizing the resulting reaction product according to the following reaction scheme.

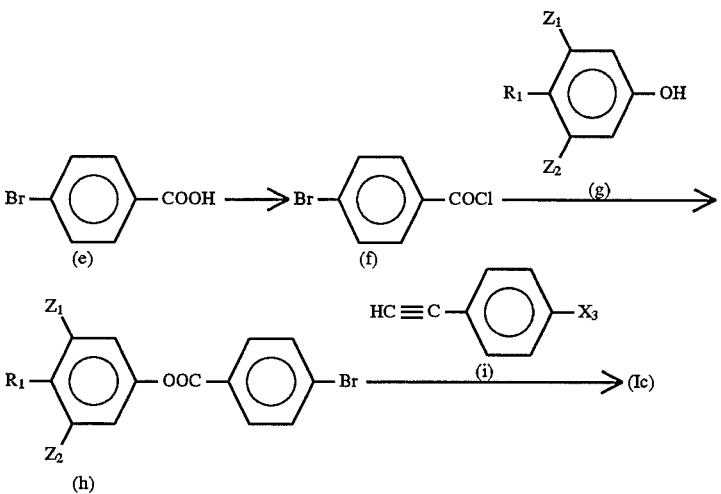

wherein $R_1$, $X_3$, $Z_1$, and $Z_2$ have the same meaning defined above.

Other features of the invention will become apparent in the course of the following description of the exemplary embodiments which are given for illustration of the invention and are not intended to be limiting thereof. In the examples below, the threshold voltage Vth was measured on the liquid crystal composition mounted on a TN-type liquid crystal display device with a cell thickness of 9 μm.

EXAMPLES

Example 1

120 g of thionyl chloride was added to 100 g of 4-bromobenzoic acid and the mixture was heated at 90° C. while stirring for 6 hours. After the reaction, an excess amount of thionyl chloride was removed by evaporation. 85 g of bromobenzoic acid chloride was obtained at a distillation temperature range of 190°–200° C. by vacuum distillation at about 20 mmHg. A solution prepared from 50 g of 3,4-difluorophenol, 150 ml of dimethylformamide, and 31 g of pyridine was added dropwise to the bromobenzoic acid chloride over about one hour while stirring at a temperature below 30° C. The mixture was then heated to 70° C. and stirred for 10 hours, and poured into a 10-fold amount of water to produce crystals. The crystals were collected by filtration, washed with dilute HCl and then water, dried in vacuum at 40° C., and recrystallized from ethyl acetate to obtain 50 g of 3,4-difluorophenyl 4-bromobenzoate. To this were added 25 g of 4-n-propylphenylacetylene, 0.11 g of bis(triphenylphosphine)palladium(II) chloride, 0.12 g of copper iodide, 0.96 g of triphenylphosphine, and 320 ml of triethylamine, followed by stirring for 10 hours while heating at 90° C. After the reaction, the reaction product was poured into a 10-fold amount of water to produce crystals. The crystals were collected by filtration, washed with water, dried in vacuum at 40° C., and recrystallized from a mixed solvent of ethyl acetate and methanol to obtain 43 g of 3,4-difluorophenyl 4-[2-(4-propylphenyl)ethynyl]benzoate of the following formula.

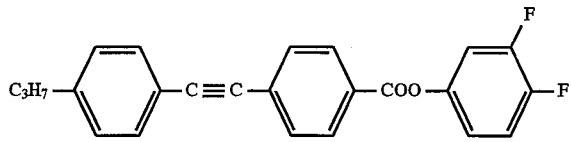

This compound had a nematic liquid crystal phase, a C-N point (crystal-nematic phase transfer temperature) of 106.9° C., and an N-I point of 168.5° C. The IR spectrum of this compound is shown in FIG. 1.

Example 2

43 g of 3,4-difluorophenyl 4-[2-(4-ethylphenyl)ethynyl] benzoate of the following formula was prepared in the same manner as in Example 1, except for using 26 g of 4-n-ethylphenylacetylene instead of 25 g of 4-n-propylphenylacetylene.

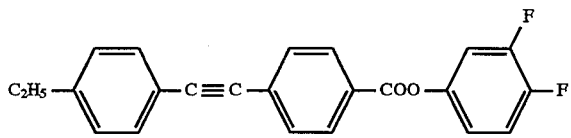

Figure 2:
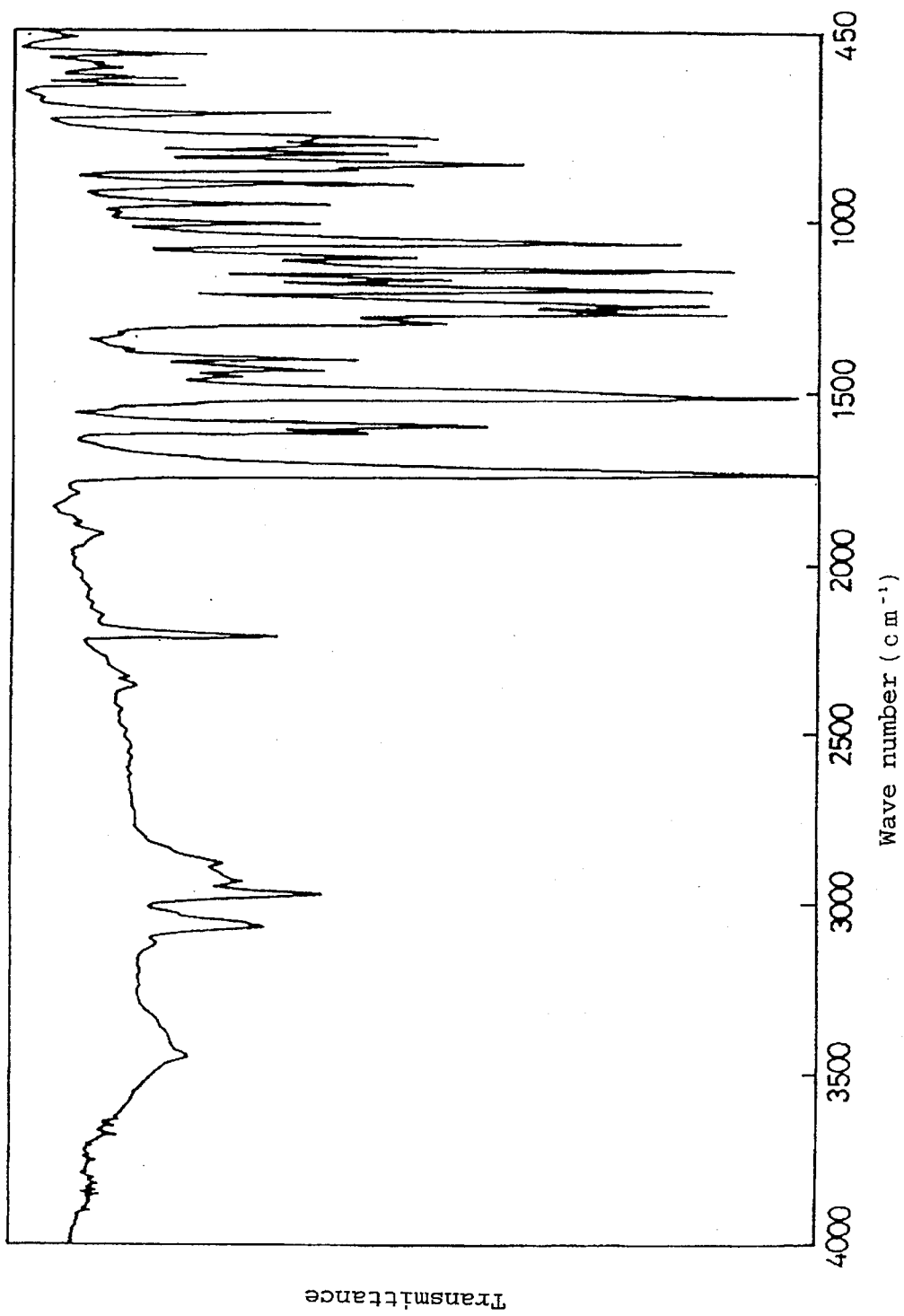
FIG. 2 is a diagram showing an infrared absorption spectrum of the tolan compound prepared in Example 2.

This compound had a nematic liquid crystal phase, a C-N point (crystal-nematic phase transfer temperature) of 113° C., and an N-I point of 162° C. The IR spectrum of this compound is shown in FIG. 2.

Example 3

43 g of 3,4-difluorophenyl 4-[2-(4-butylphenyl)ethylnyl] benzoate of the following formula was prepared in the same manner as in Example 1, except for using 24 g of 4-n-butylphenylacetylene instead of 25 g of 4-n-propylphenylacetylene.

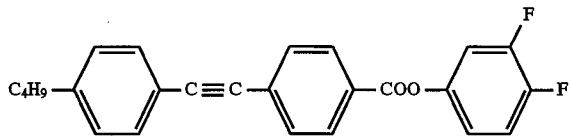

Figure 3:
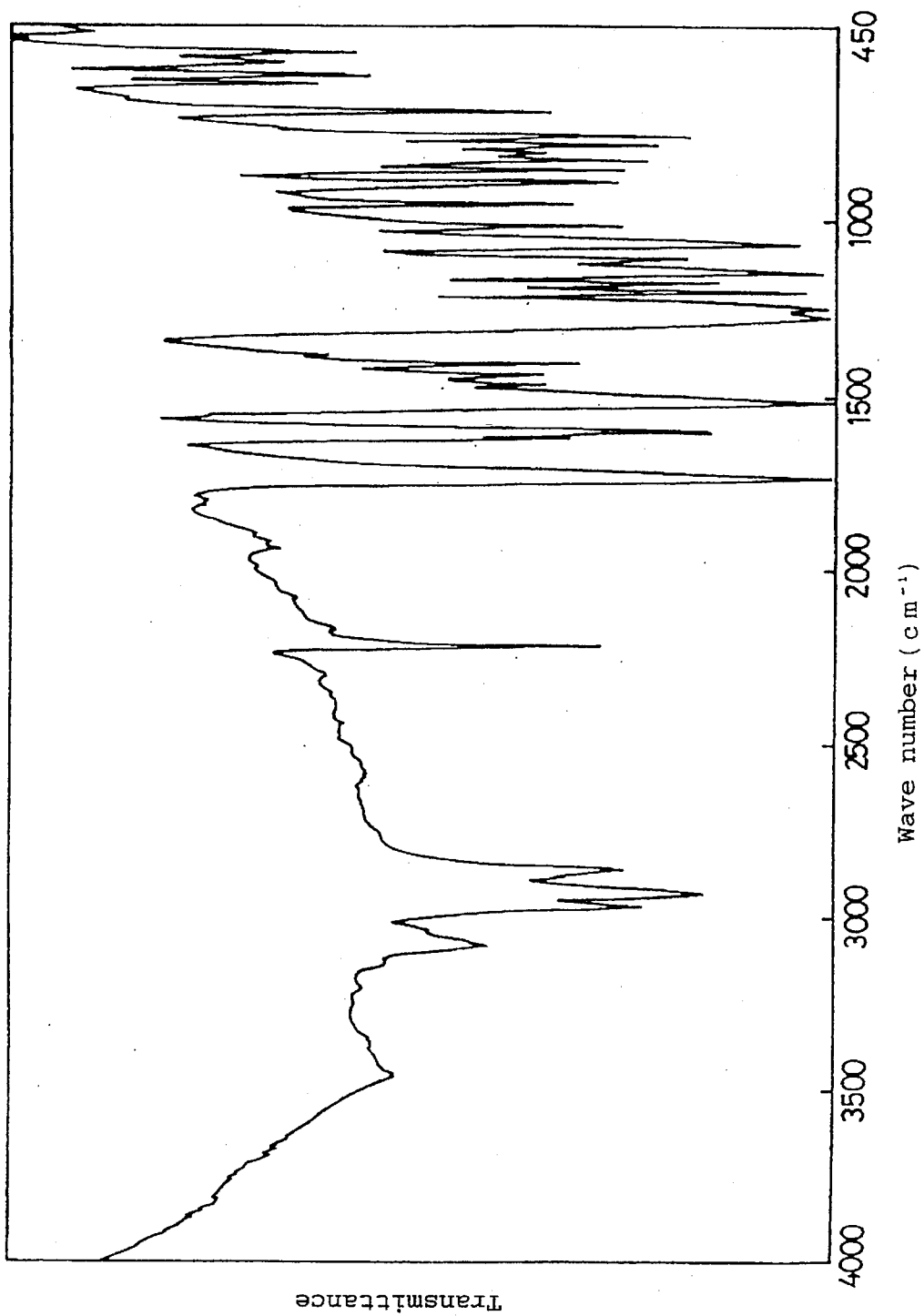
FIG. 3 is a diagram showing an infrared absorption spectrum of the tolan compound prepared in Example 3.

This compound had a liquid crystal phase, a C-S point (crystal-smectic phase transfer temperature) of 89° C., an S-N point (smectic-nematic phase transfer temperature) of 115° C., and an N-I point of 157° C. The IR spectrum of this compound is shown in FIG. 3.

Example 4

43 g of 3,4-difluorophenyl 4-[2-(4-pentylphenyl)ethynyl] benzoate of the following formula was prepared in the same manner as in Example 1, except for using 23 g of 4-n-pentylphenylacetylene instead of 25 g of 4-n-propylphenylacetylene.

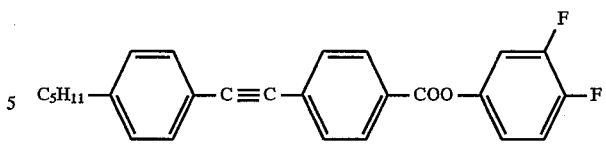

Figure 4:
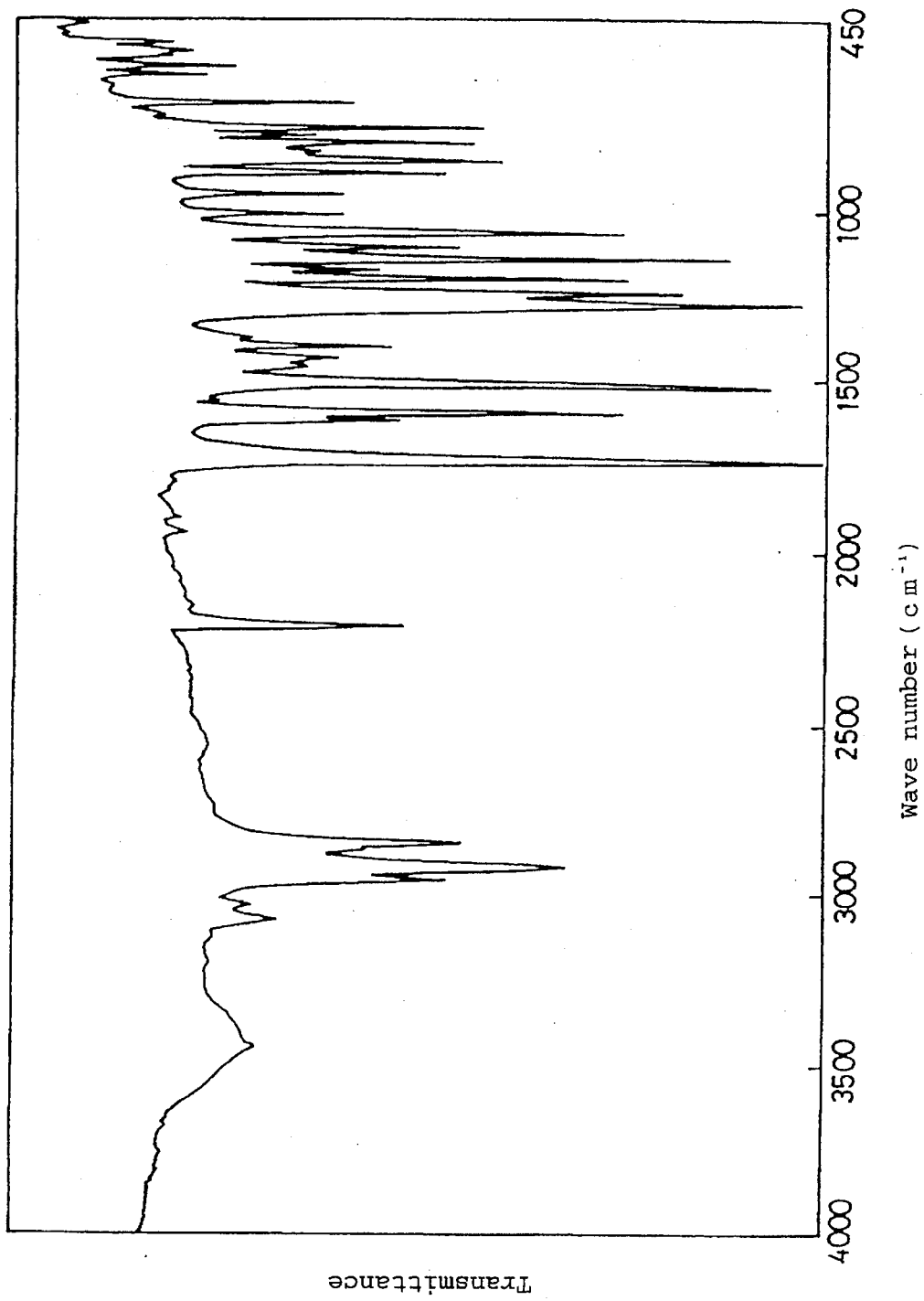
FIG. 4 is a diagram showing an infrared absorption spectrum of the tolan compound prepared in Example 4.

This compound had a liquid crystal phase, a C-S point (crystal-smectic phase transfer temperature) of 88° C., an S-N point (smectic-nematic phase transfer temperature) of 122° C., and an N-I point of 160° C. The IR spectrum of this compound is shown in FIG. 4.

Example 5

38 g of 4-fluorophenyl 4-[2-(4-propylphenyl)ethynyl] benzoate of the following formula was prepared in the same manner as in Example 1, except for using 43g of 4-fluorophenol instead of 50 g of 3,4-difluorophenol.

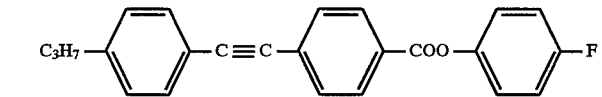

Figure 5:
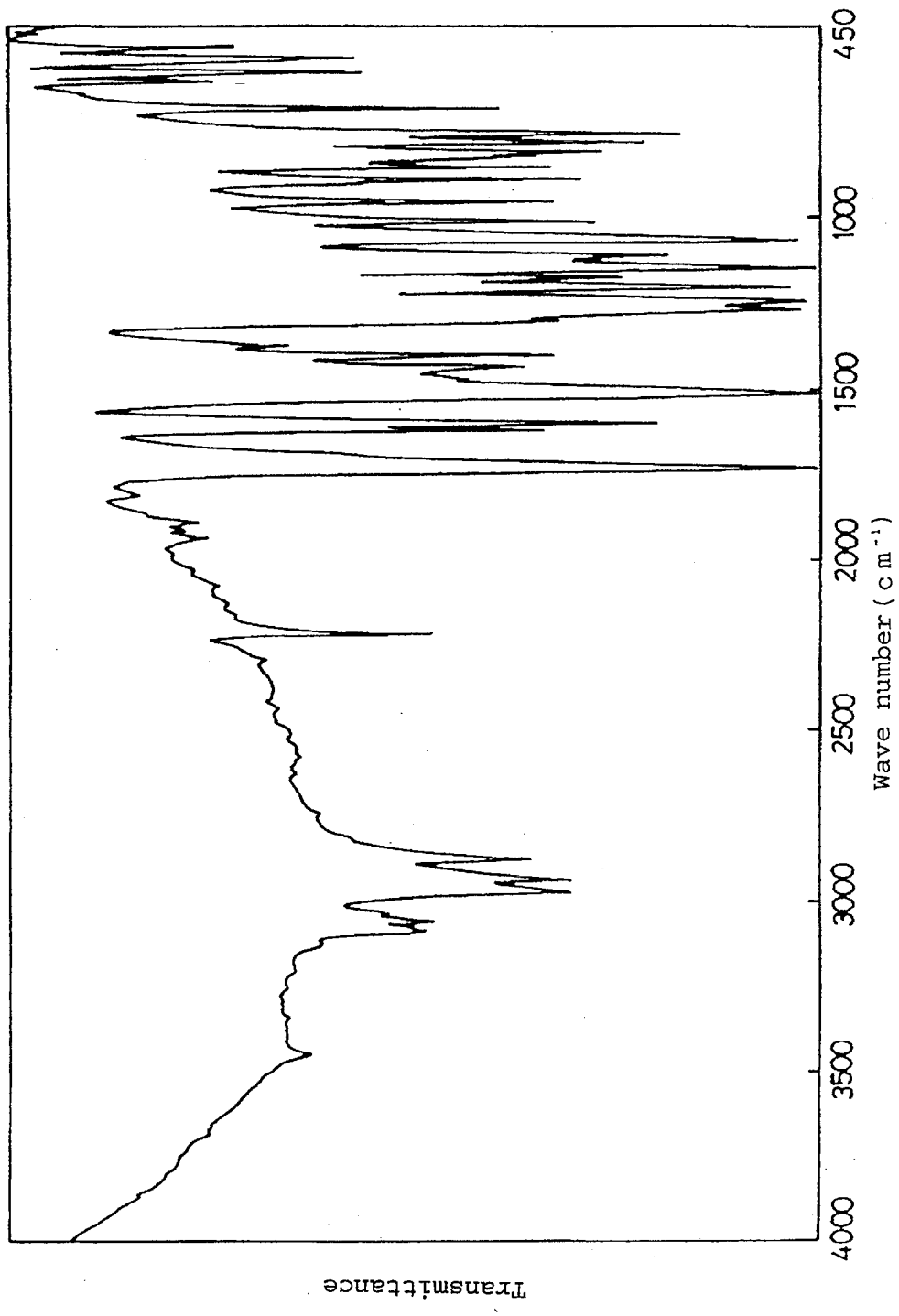
FIG. 5 is a diagram showing an infrared absorption spectrum of the tolan compound prepared in Example 5.

This compound had a nematic liquid crystal phase, a C-N point (crystal-nematic phase transfer temperature) of 131° C., and an N-I point of 199° C. The IR spectrum of this compound is shown in FIG. 5.

Example 6

40 g of 4-cyanophenyl 4-[2-(4-propylphenyl)ethynyl] benzoate of the following formula was prepared in the same manner as in Example 1, except for using 46 g of 4-cyanophenol instead of 50 g of 3,4-difluorophenol.

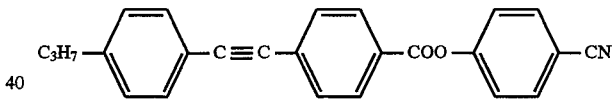

Figure 6:
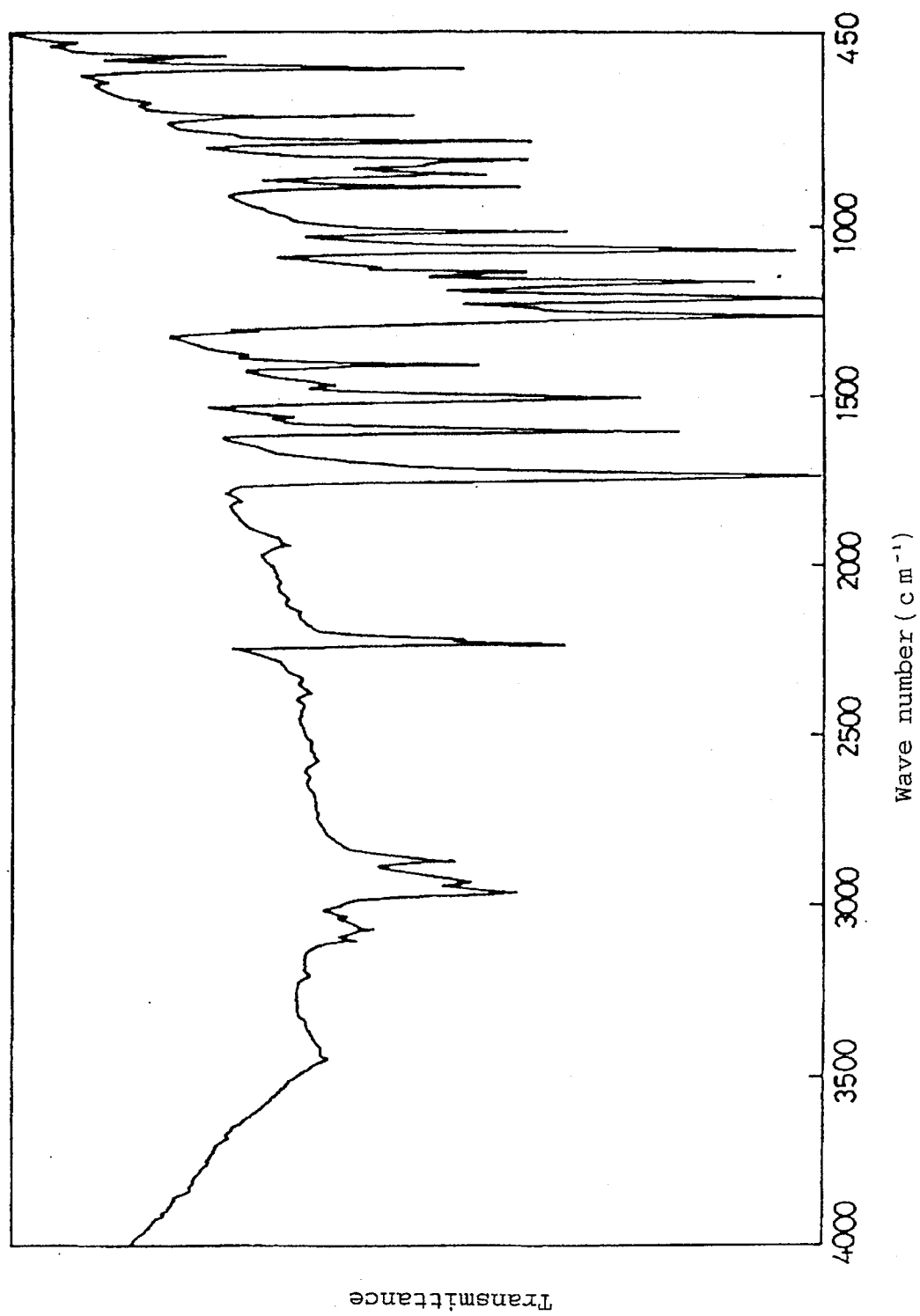
FIG. 6 is a diagram showing an infrared absorption spectrum of the tolan compound prepared in Example 6.

This compound had a nematic liquid crystal phase, a C-N point (crystal-nematic phase transfer temperature) of 140° C., and an N-I point of 268° C. The IR spectrum of this compound is shown in FIG. 6.

Example 7

45 g of 4-ethoxyphenyl 4-[2-(4-propylphenyl)ethynyl] benzoate of the following formula was prepared in the same manner as in Example 1, except for using 53 g of 4-ethoxyphenol instead of 50 g of 3,4-difluorophenol.

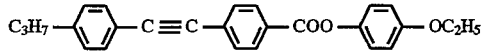

Figure 7:
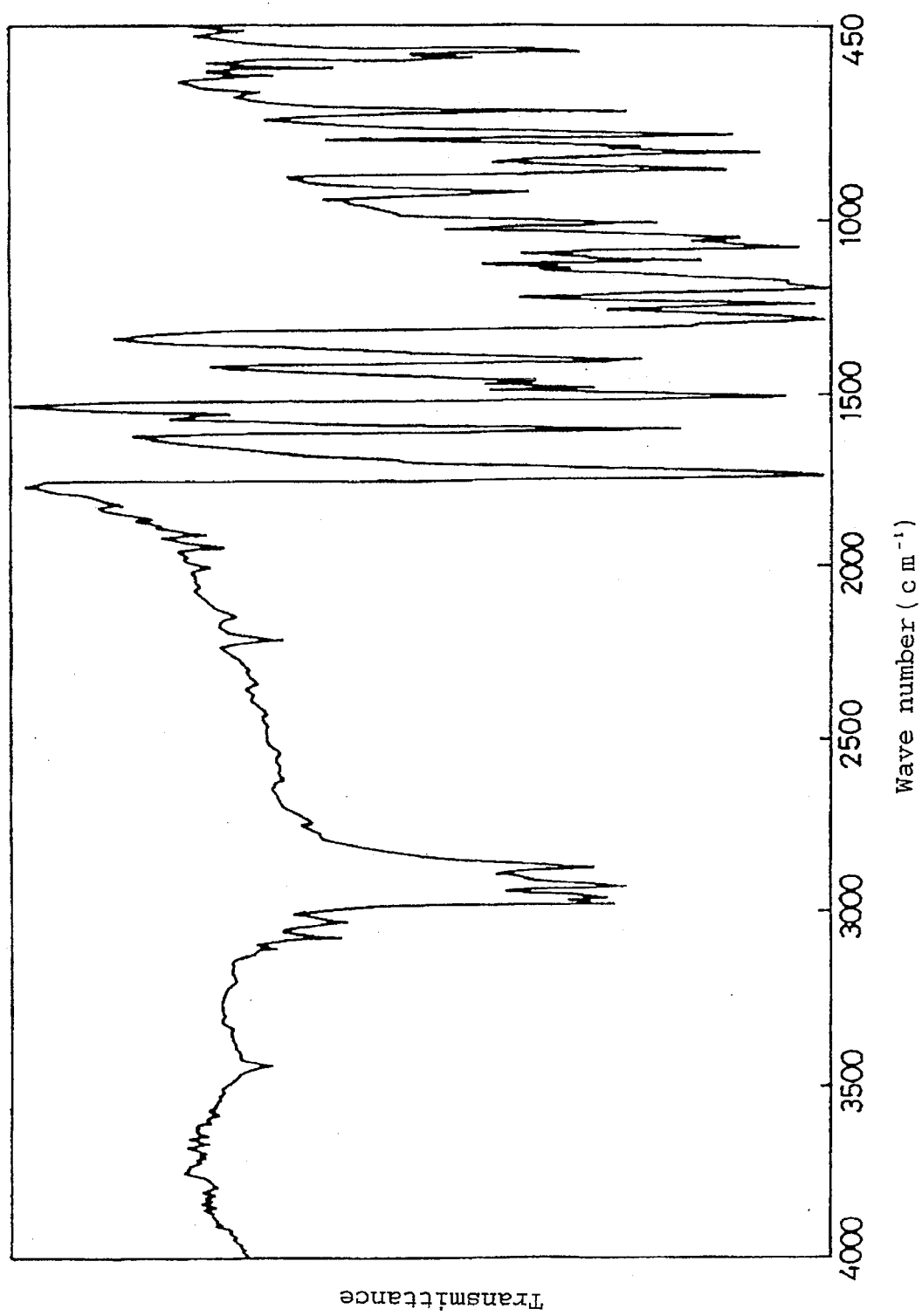
FIG. 7 is a diagram showing an infrared absorption spectrum of the tolan compound prepared in Example 7.

This compound had a nematic liquid crystal phase, a C-N point (crystal-nematic phase transfer temperature) of 113° C., and an N-I point of 254° C. The IR spectrum of this compound is shown in FIG. 7.

Example 8

44 g of 4-propylphenyl 4-[2-(4-propylphenyl)ethynyl] benzoate of the following formula was prepared in the same manner as in Example 1, except for using 52 g of 4-propylphenol instead of 50 g of 3,4-difluorophenol.

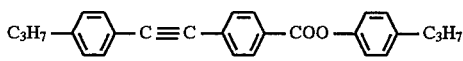

Figure 8:
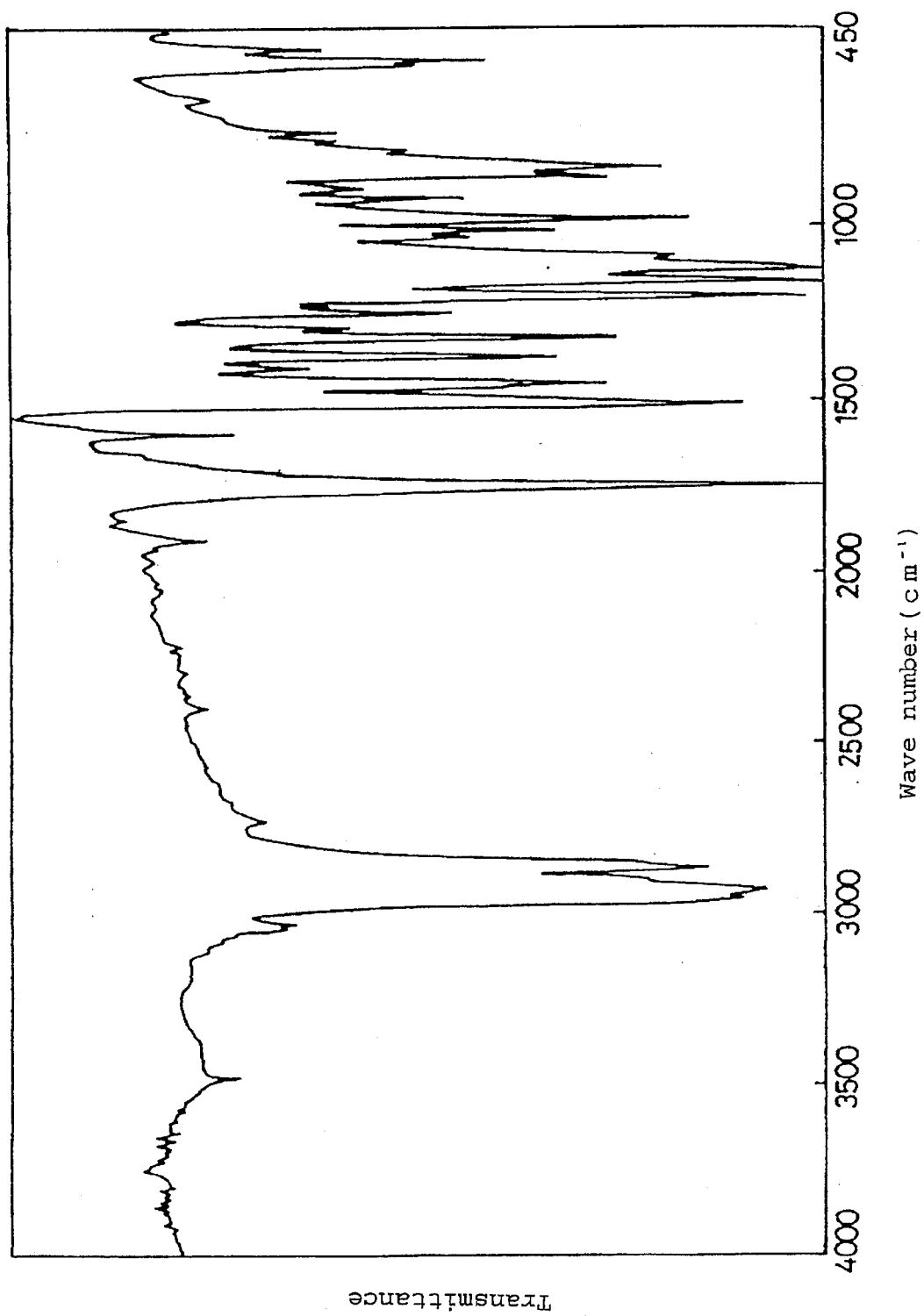
FIG. 8 is a diagram showing an infrared absorption spectrum of the tolan compound prepared in Example 8.

This compound had a nematic liquid crystal phase, a C-N point (crystal-nematic phase transfer temperature) of 130° C., and an N-I point of 211° C. The IR spectrum of this compound is shown in FIG. 8.

Example 9

35 g of 4-methylphenyl 4-[2-(4-propylphenyl)ethynyl] benzoate of the following formula was prepared in the same manner as in Example 1, except for using 41 g of 4-methylphenol instead of 50 g of 3,4-difluorophenol.

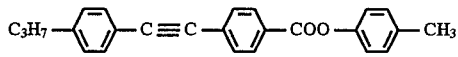

Figure 9:
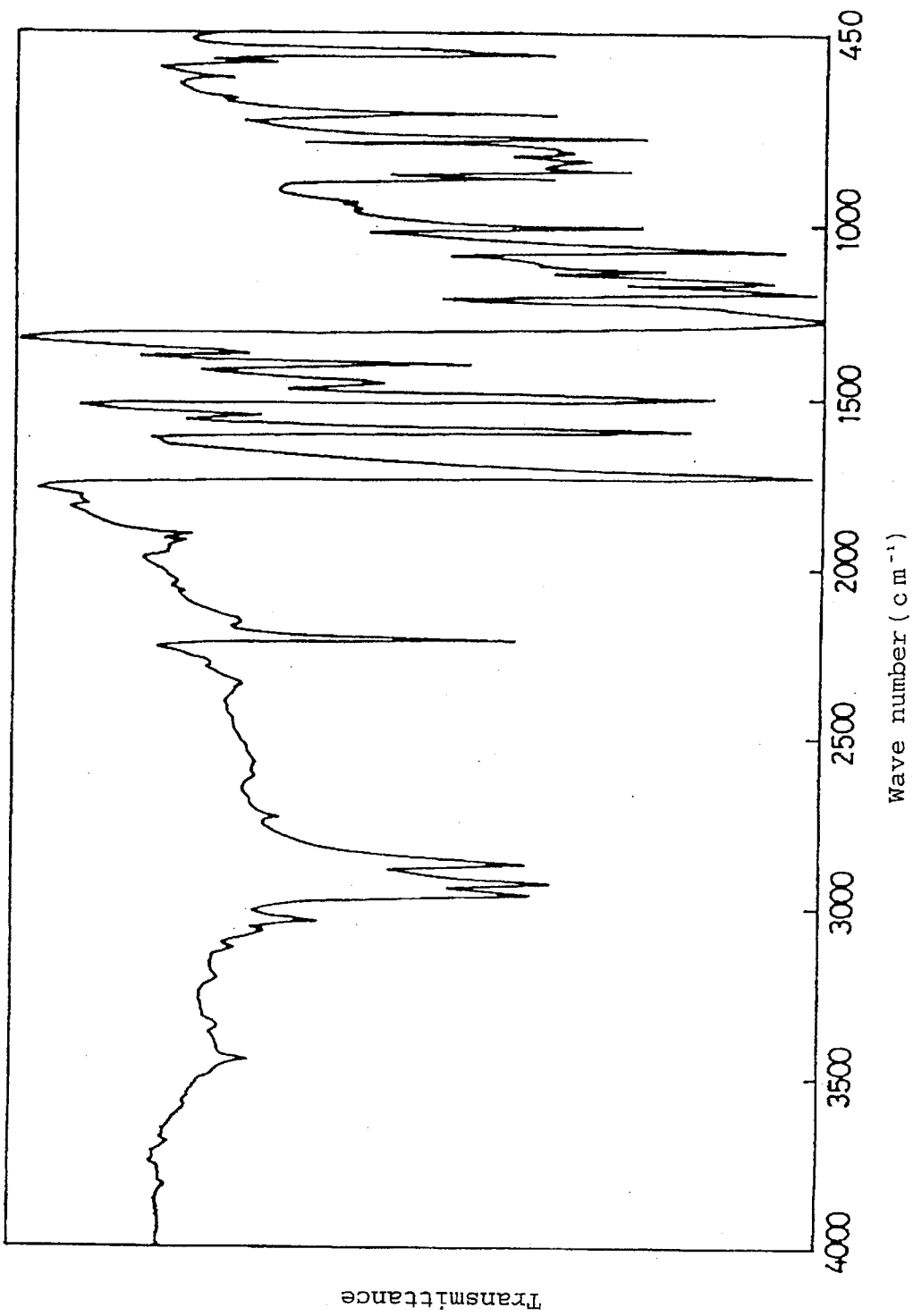
FIG. 9 is a diagram showing an infrared absorption spectrum of the tolan compound prepared in Example 9.

This compound had a nematic liquid crystal phase, a C-N point (crystal-nematic phase transfer temperature) of 124° C., and an N-I point of 219° C. The IR spectrum of this compound is shown in FIG. 9.

Example 10

34 g of 4-methylphenyl 4-[2-(4-ethylphenyl)-ethynyl] benzoate of the following formula was prepared in the same manner as in Example 1, except for using 41 g of 4-methylphenol instead of 50 g of 3,4-difluorophenol and 26 g of 4-ethylphenyl acetylene instead of 25 g of 4-n-propylphenyl acetylene.

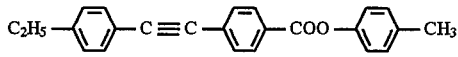

Figure 10:
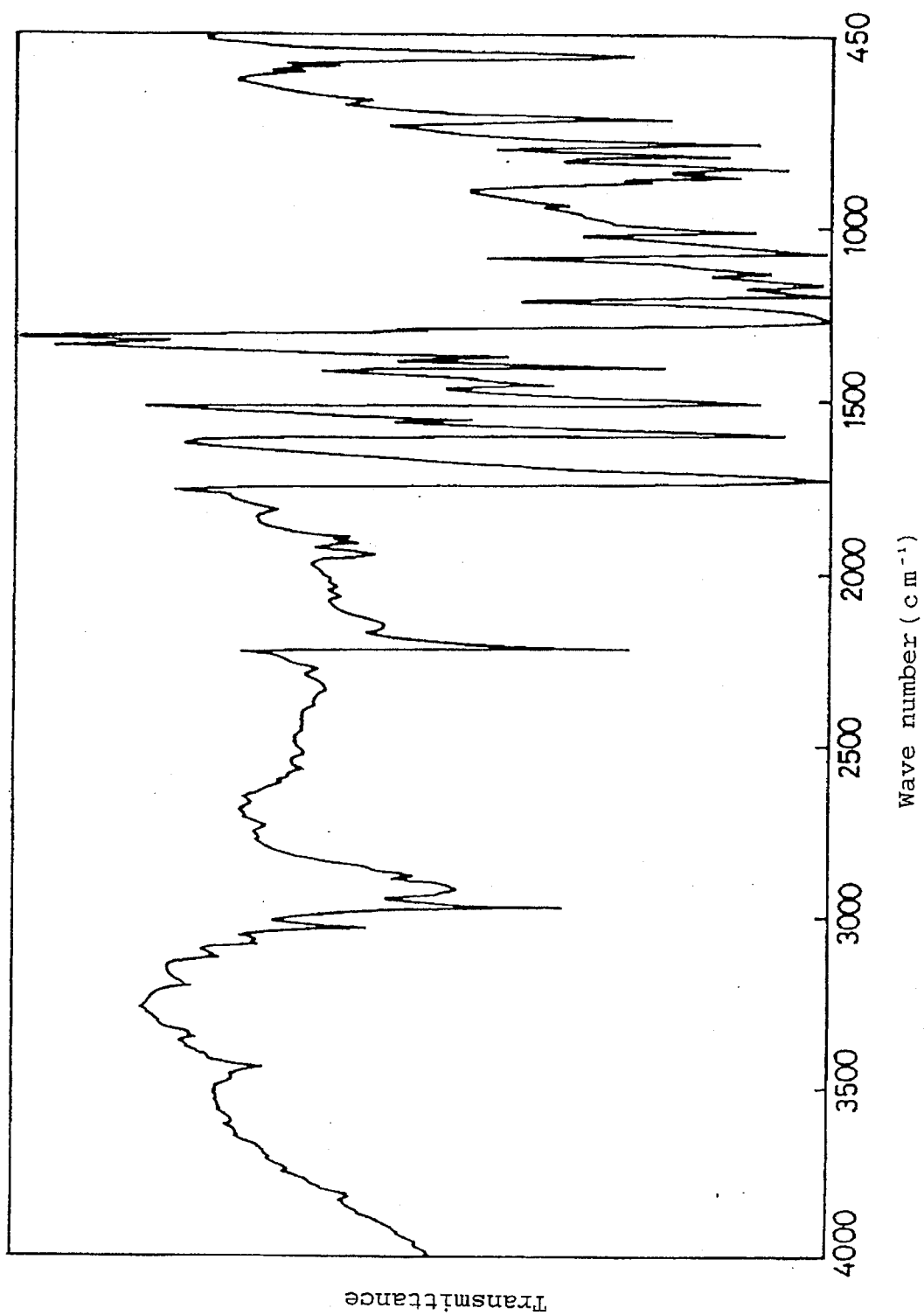
FIG. 10 is a diagram showing an infrared absorption spectrum of the tolan compound prepared in Example 10.

This compound had a nematic liquid crystal phase, a C-N point (crystal-nematic phase transfer temperature) of 121° C., and an N-I point of 215° C. The IR spectrum of this compound is shown in FIG. 10.

Example 11

34 g of 4-methylphenyl 4-[2-(4-butylphenyl)-ethynyl] benzoate of the following formula was prepared in the same manner as in Example 1, except for using 41 g of 4-methylphenol instead of 50 g of 3,4-difluorophenol and 24 g of 4-n-butylphenyl acetylene instead of 25 of 4-n-propylphenyl acetylene.

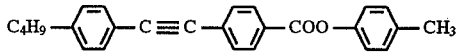

Figure 11:
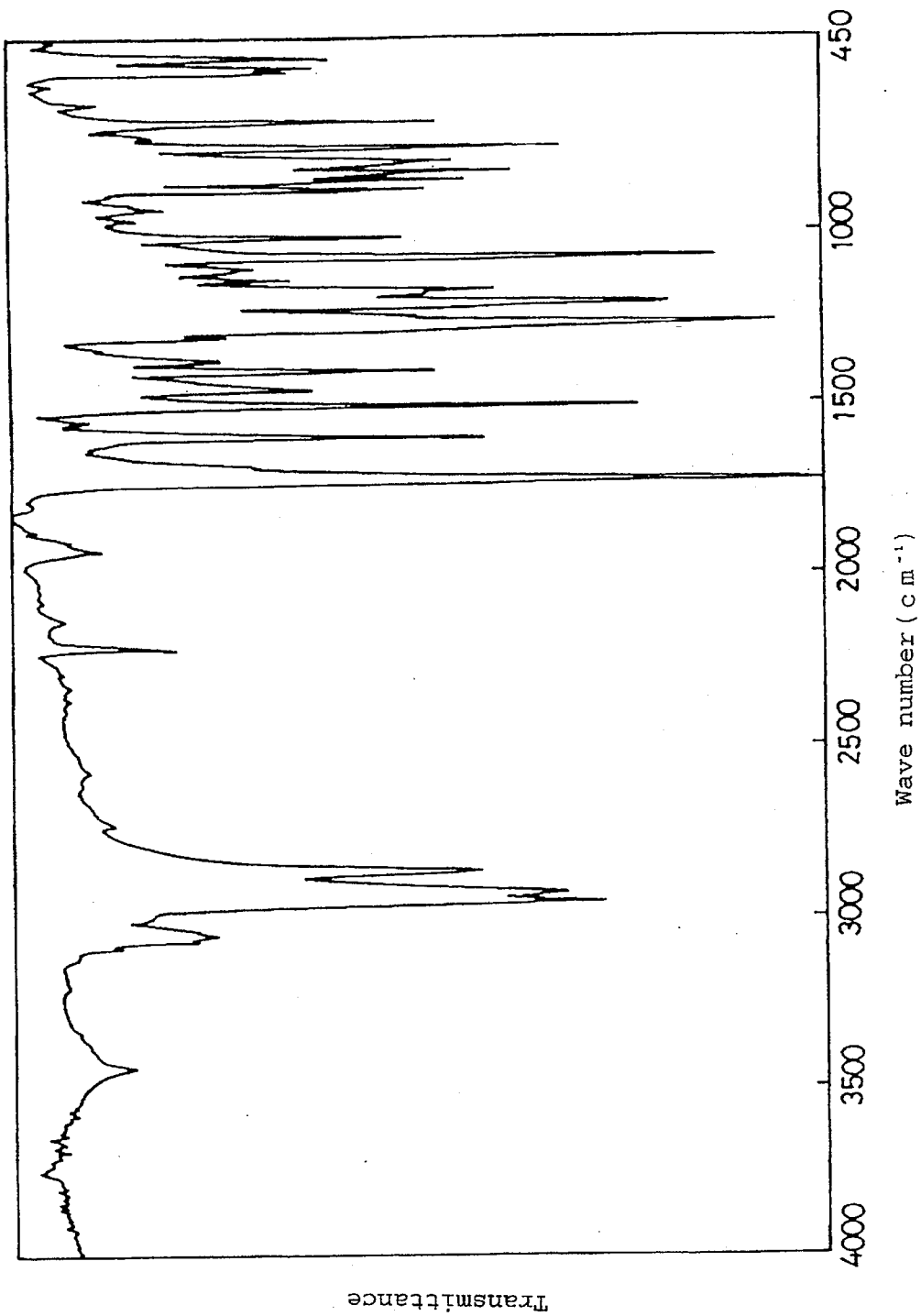
FIG. 11 is a diagram showing an infrared absorption spectrum of the tolan compound prepared in Example 11.

This compound had a nematic liquid crystal phase, a C-N point (crystal-nematic phase transfer temperature) of 107° C., and an N-I point of 203° C. The IR spectrum of this compound is shown in FIG. 11.

Example 12

33 g of 4-methylphenyl 4-[2-(4-pentylphenyl)ethynyl] benzoate of the following formula was prepared in the same manner as in Example 1, except for using 41 g of 4-methylphenol instead of 50 g of 3,4-difluorophenol and 23 g of 4-n-pentylphenyl acetylene instead of 25 g of 4-n-propylphenyl acetylene.

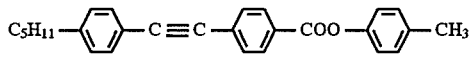

Figure 12:
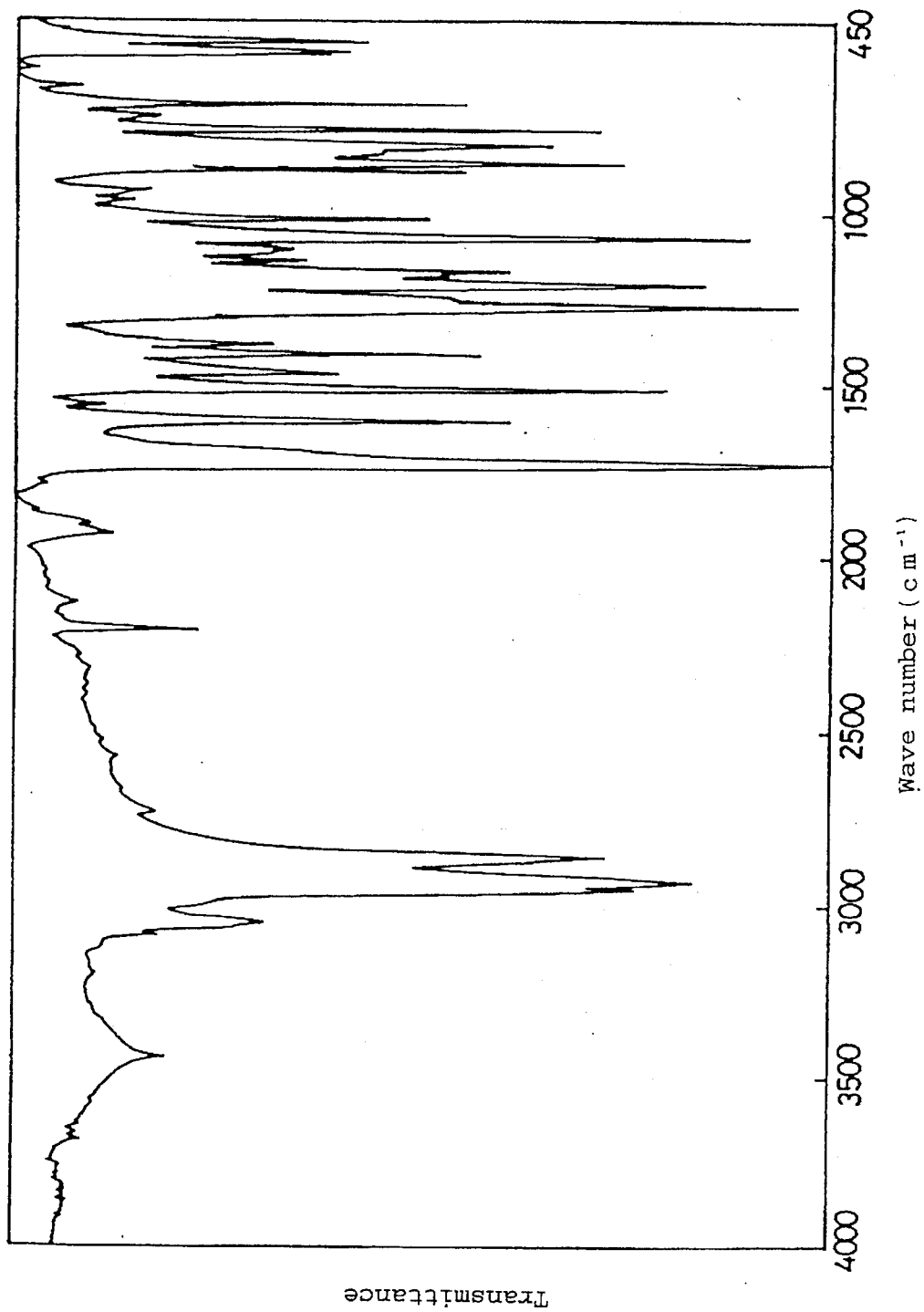
FIG. 12 is a diagram showing an infrared absorption spectrum of the tolan compound prepared in Example 12.

This compound had a nematic liquid crystal phase, a C-N point (crystal-nematic phase transfer temperature) of 110° C., and an N-I point of 202° C. The IR spectrum of this compound is shown in FIG. 12.

Example 13

35 g of 3-fluoro-4-cyanophenyl 4-[2-(4-propylphenyl) ethynyl]benzoate of the following formula was prepared in the same manner as in Example 1, except for using 51 g of 3-fluoro-4-cyanophenol instead of 50 g of 3,4-difluorophenol.

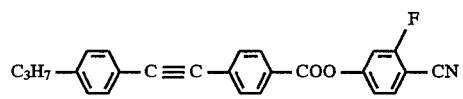

Figure 13:
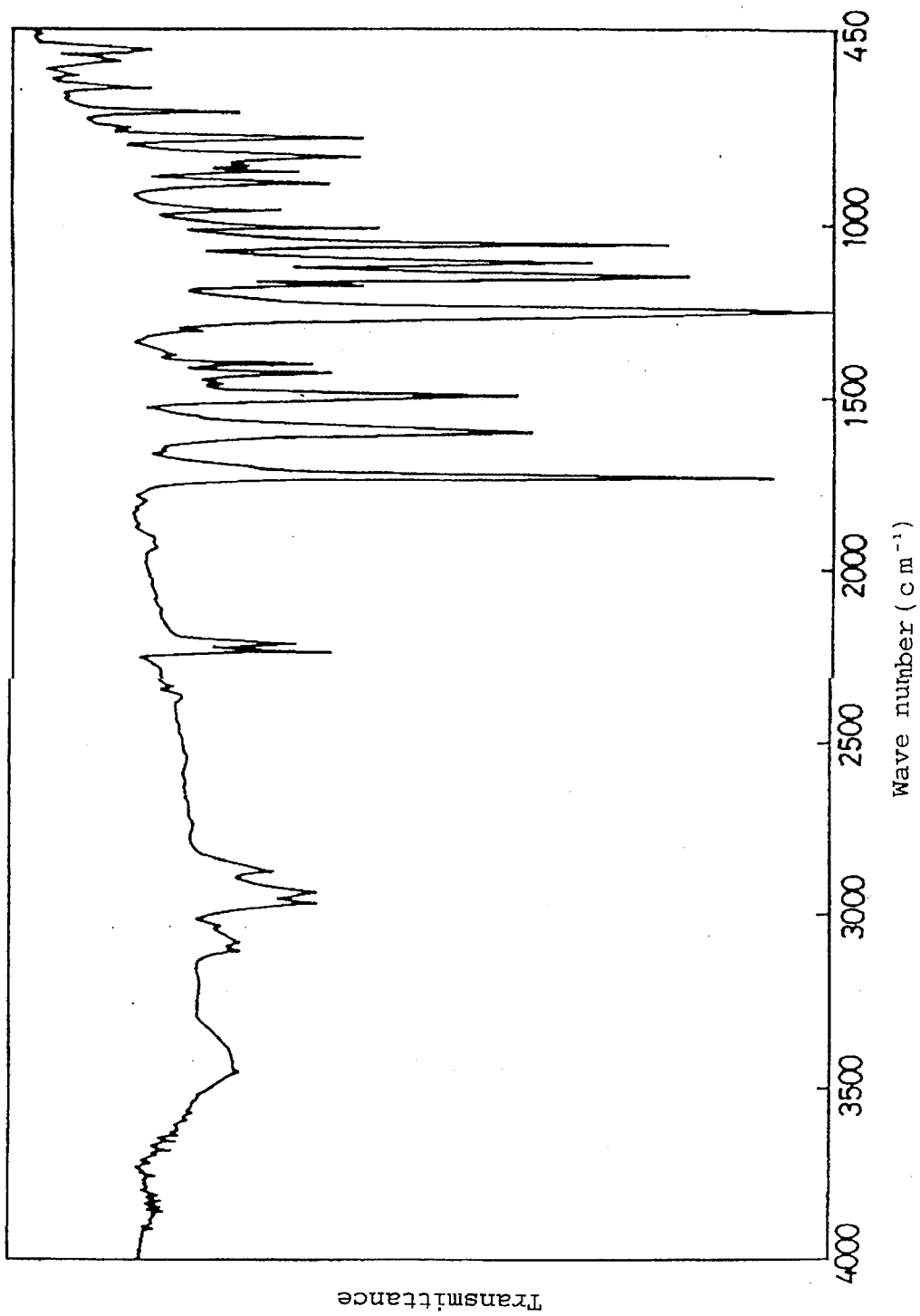
FIG. 13 is a diagram showing an infrared absorption spectrum of the tolan compound prepared in Example 13.

This compound had a nematic liquid crystal phase, a C-N point (crystal-nematic phase transfer temperature) of 87° C., and an N-I point of 229° C. The IR spectrum of this compound is shown in FIG. 13.

Example 14

A liquid crystal composition was prepared by blending 90 parts by weight of a commercially available nematic liquid crystal composition, ZLI-1132™ (a product of Merck), and 10 parts of the tolan compound of the present invention prepared in Example 1. The properties of the liquid crystal composition were measured and the composition was found to have the following properties:

NI point: 78.0° C.

Δn: 0.153

Viscosity: 30.5 cP

Vth: 1.78 V

The properties of the liquid crystal composition, ZLI-1132™, were as follows:

NI point: 72° C.

Δn: 0.138

Viscosity: 27.9 cP

Vth: 1.83 V

Examples 15–26

Liquid crystal compositions were prepared in the same manner as in Example 14 from 90 parts by weight of the liquid crystal composition ZLI-1132™ and 10 parts by weight of the tolan compounds of the present invention prepared in Examples 2–13. The properties of these liquid crystal compositions and the chemical formulas of the tolan compounds of the present invention used for these compositions are given in Tables 1 and 2. These tables include the corresponding data for the liquid crystal composition of Example 14 and the properties of the liquid crystal composition ZLI-1132™.

TABLE 1

| Example No. | Chemical Formula | N-I Point (°C.) | Δn at 25° C. | Viscosity (cP) at 20° C. | Vth (V) at 25° C. |
|---|---|---|---|---|---|
| 14 | $C_3H_7$—⟨◯⟩—C≡C—⟨◯⟩—COO—⟨◯⟩(F)—F | 78.0 | 0.153 | 30.5 | 1.78 |
| 15 | $C_2H_5$—⟨◯⟩—C≡C—⟨◯⟩—COO—⟨◯⟩(F)—F | 78.3 | 0.153 | 30.2 | 1.70 |
| 16 | $C_4H_9$—⟨◯⟩—C≡C—⟨◯⟩—COO—⟨◯⟩(F)—F | 78.5 | 0.148 | 31.2 | 1.65 |
| 17 | $C_5H_{11}$—⟨◯⟩—C≡C—⟨◯⟩—COO—⟨◯⟩(F)—F | 79.1 | 0.151 | 31.3 | 1.72 |
| 18 | $C_3H_7$—⟨◯⟩—C≡C—⟨◯⟩—COO—⟨◯⟩—F | 78.5 | 0.154 | 29.9 | 1.80 |
| 19 | $C_3H_7$—⟨◯⟩—C≡C—⟨◯⟩—COO—⟨◯⟩—CN | 79.7 | 0.150 | 31.4 | 1.82 |
| 20 | $C_3H_7$—⟨◯⟩—C≡C—⟨◯⟩—COO—⟨◯⟩—$OC_2H_5$ | 84.8 | 0.157 | 31.1 | 1.91 |

TABLE 2

| Example No. | Chemical Formula | N-I Point (°C.) | Δn at 25° C. | Viscosity (cP) at 20° C. | Vth (V) at 25° C. |
|---|---|---|---|---|---|
| 21 | $C_3H_7$—⟨◯⟩—C≡C—⟨◯⟩—COO—⟨◯⟩—$C_3H_7$ | 81.9 | 0.155 | 29.5 | 1.87 |
| 22 | $C_3H_7$—⟨◯⟩—C≡C—⟨◯⟩—COO—⟨◯⟩—$CH_3$ | 83.6 | 0.155 | 30.3 | 1.85 |
| 23 | $C_2H_5$—⟨◯⟩—C≡C—⟨◯⟩—COO—⟨◯⟩—$CH_3$ | 83.5 | 0.157 | 30.0 | 1.84 |
| 24 | $C_4H_9$—⟨◯⟩—C≡C—⟨◯⟩—COO—⟨◯⟩—$CH_3$ | 82.4 | 0.155 | 30.0 | 1.86 |
| 25 | $C_5H_{11}$—⟨◯⟩—C≡C—⟨◯⟩—COO—⟨◯⟩—$CH_3$ | 82.6 | 0.153 | 30.3 | 1.89 |
| 26 | $C_3H_7$—⟨◯⟩—C≡C—⟨◯⟩—COO—⟨◯⟩(F)—CN | 84.1 | 0.159 | 34.7 | 1.73 |
| ZLI-1132 | | 72.0 | 0.138 | 27.9 | 1.83 |

As can be seen from Tables 1 and 2, the tolan compounds of the present invention increase the N-I point and double refractive index (Δn) of the liquid crystal compositions which contain these compounds, and some of these compounds decrease the threshold voltage Vth of such compositions. The tolan compounds of the present invention are thus effective as a component for liquid crystal compositions.

Example 27

20 g of 4-bromophenylphenol, 150 ml of dimethylformamide, and 6 g of pyridine were dissolved 15 g of commercially available trans-4-n-butylcyclohexanone carboxylic acid chloride was added dropwise to the solution and the mixture was heated while stirring. The reaction mixture was poured into water to produce crystals. The crystals were collected by filtration, washed with dilute HCl and then water, dried in vacuum, and recrystallized from a mixed solvent of ethyl acetate and methanol to obtain 20 g of 4-bromo-4'-biphenyl trans-4-n-butylcyclohexane carboxylate. To this were added 7 g of 4-ethylphenyl-acetylene, 0.03 g of bis(triphenylphosphine)-palladium(II) chloride, 0.04 g of copper iodide, 0.3 g of triphenylphosphine, and 100 ml of triethylamine, and the mixture was heated while stirring. After the reaction, the reaction product was poured into water and neutralized with HCl to produce crystals. The crystals were collected by filtration, washed with water, dried in vacuum, and recrystallized from a mixed solvent of ethyl acetate and methanol to obtain 12.5 g of a compound having the following formula.

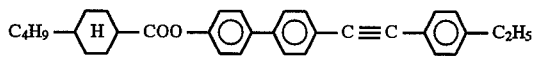

Figure 14:
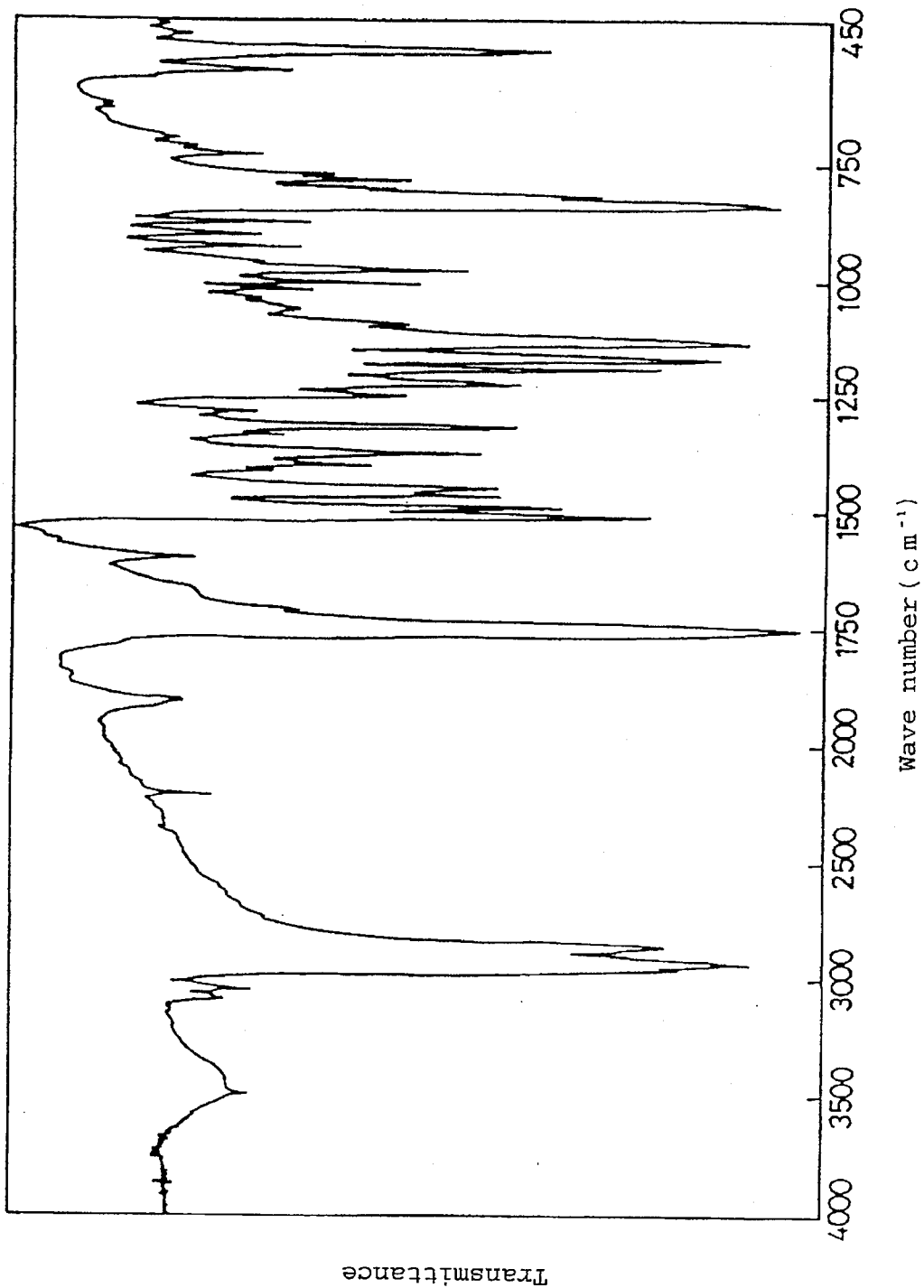
FIG. 14 is a diagram showing an infrared absorption spectrum of the tolan compound prepared in Example 27.

This compound had a nematic liquid crystal phase, a C-N point (crystal-nematic phase transfer temperature) of 213° C., and an N-I point of 226° C. The IR spectrum of this compound is shown in FIG. 14.

Example 28

13 g of a compound having the following formula was prepared in the same manner as in Example 27, except for using 8 g of 4-n-propylphenyl acetylene instead of 7 g of 4-ethylphenyl acetylene.

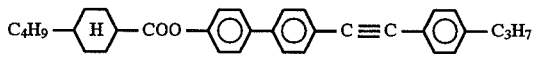

Figure 15:
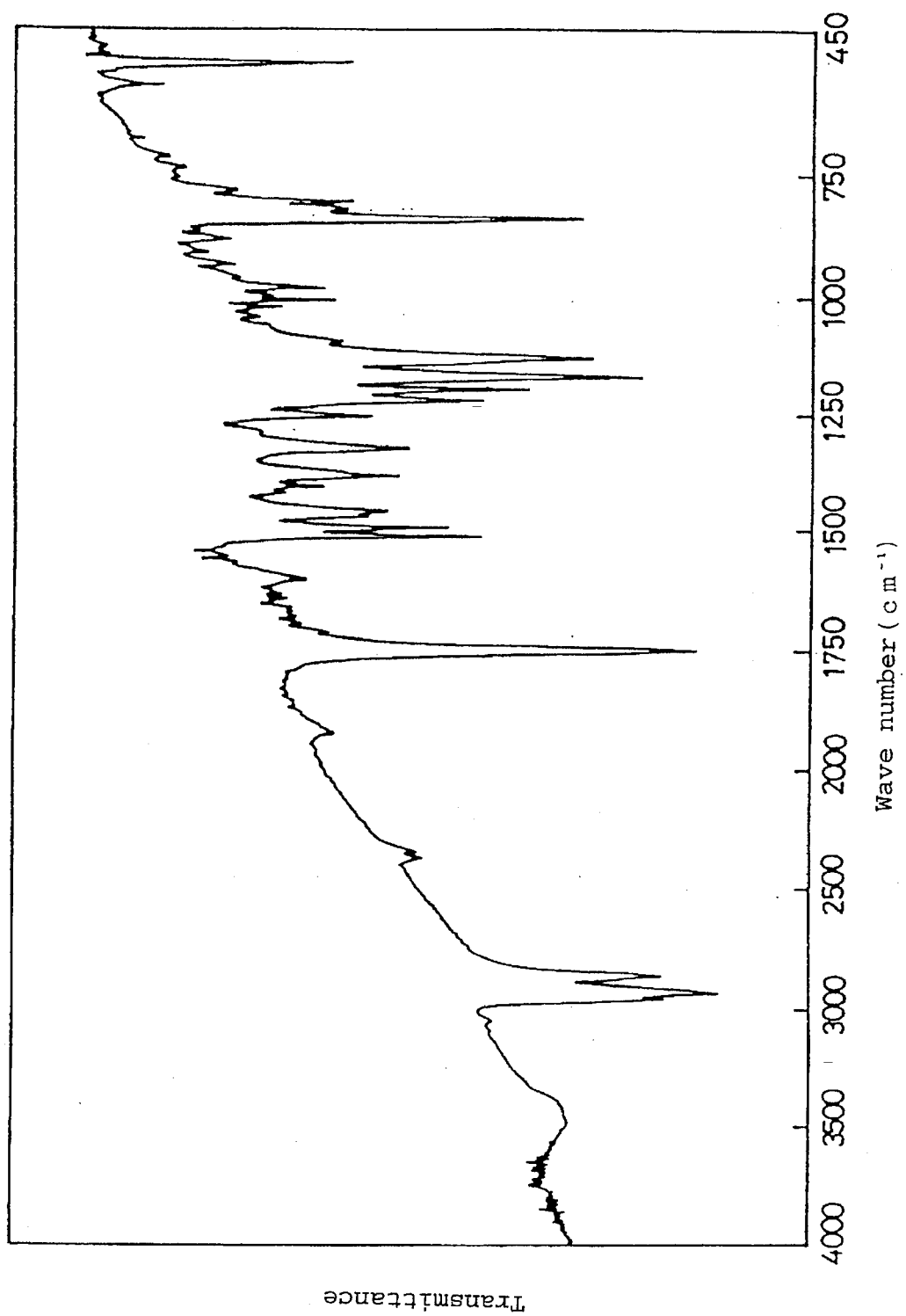
FIG. 15 is a diagram showing an infrared absorption spectrum of the tolan compound prepared in Example 28.

This compound had a nematic liquid crystal phase, a C-N point of 209° C., and an N-I point of 224° C. The IR spectrum of this compound is shown in FIG. 15.

Example 29

12 g of a compound having the following formula was prepared in the same manner as in Example 27, except for using 6 g of 4-fluorophenyl acetylene instead of 7 g of 4-ethylphenyl acetylene.

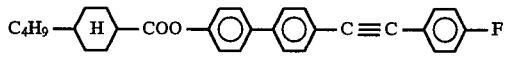

Figure 16:
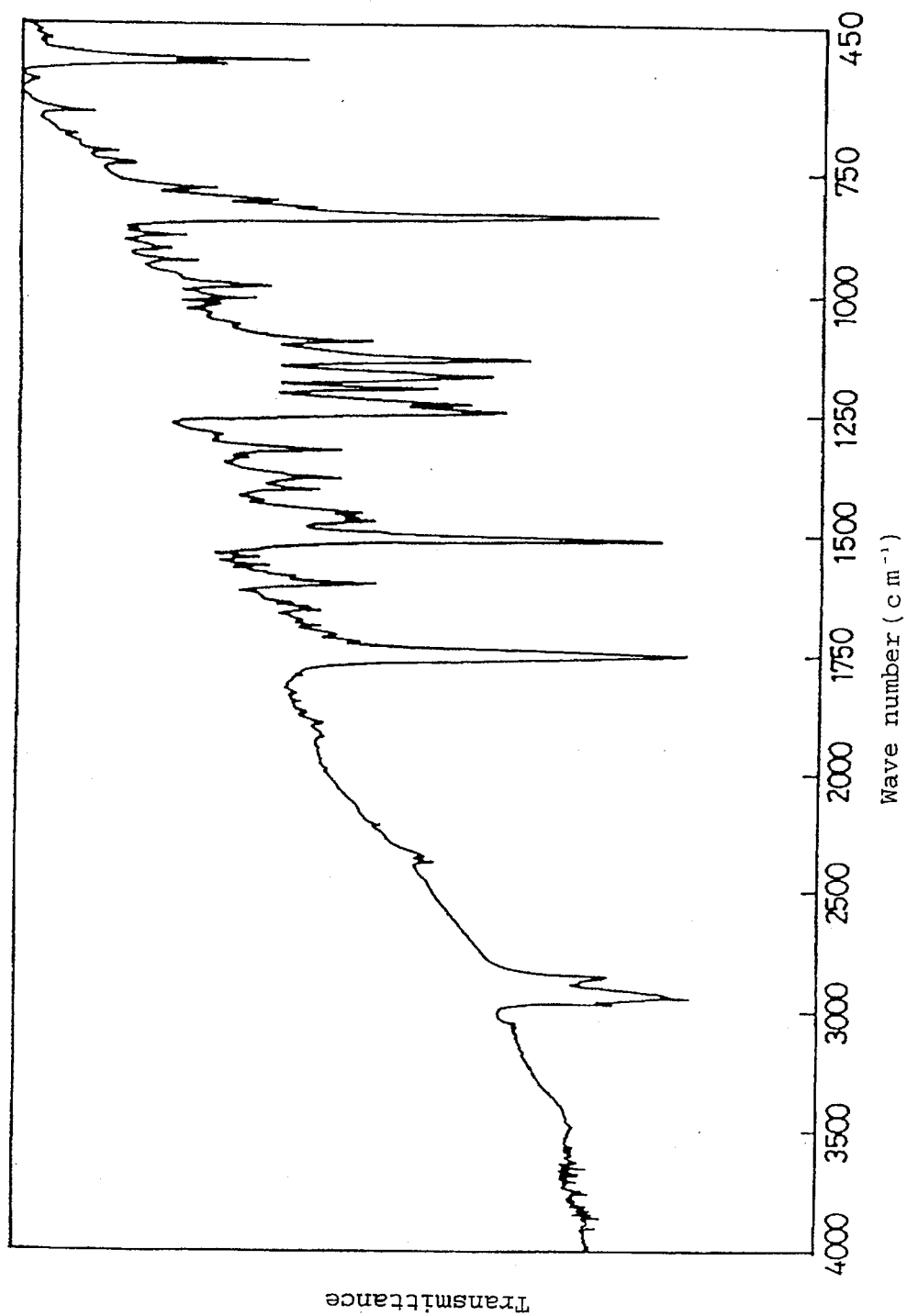
FIG. 16 is a diagram showing an infrared absorption spectrum of the tolan compound prepared in Example 29.

This compound had a nematic liquid crystal phase, a C-N point of 209° C., and an N-I point of 237° C. The IR spectrum of this compound is shown in FIG. 16.

Example 30

14 g of a compound having the following formula was prepared in the same manner as in Example 27, except for using 14 g of 4-bromophenol instead of 20 g of 4-bromophenylphenol and further using 11 g of 4-n-heptylbiphenyl acetylene instead of 7 g of 4-ethylphenyl acetylene.

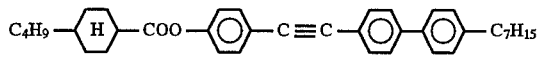

Figure 17:
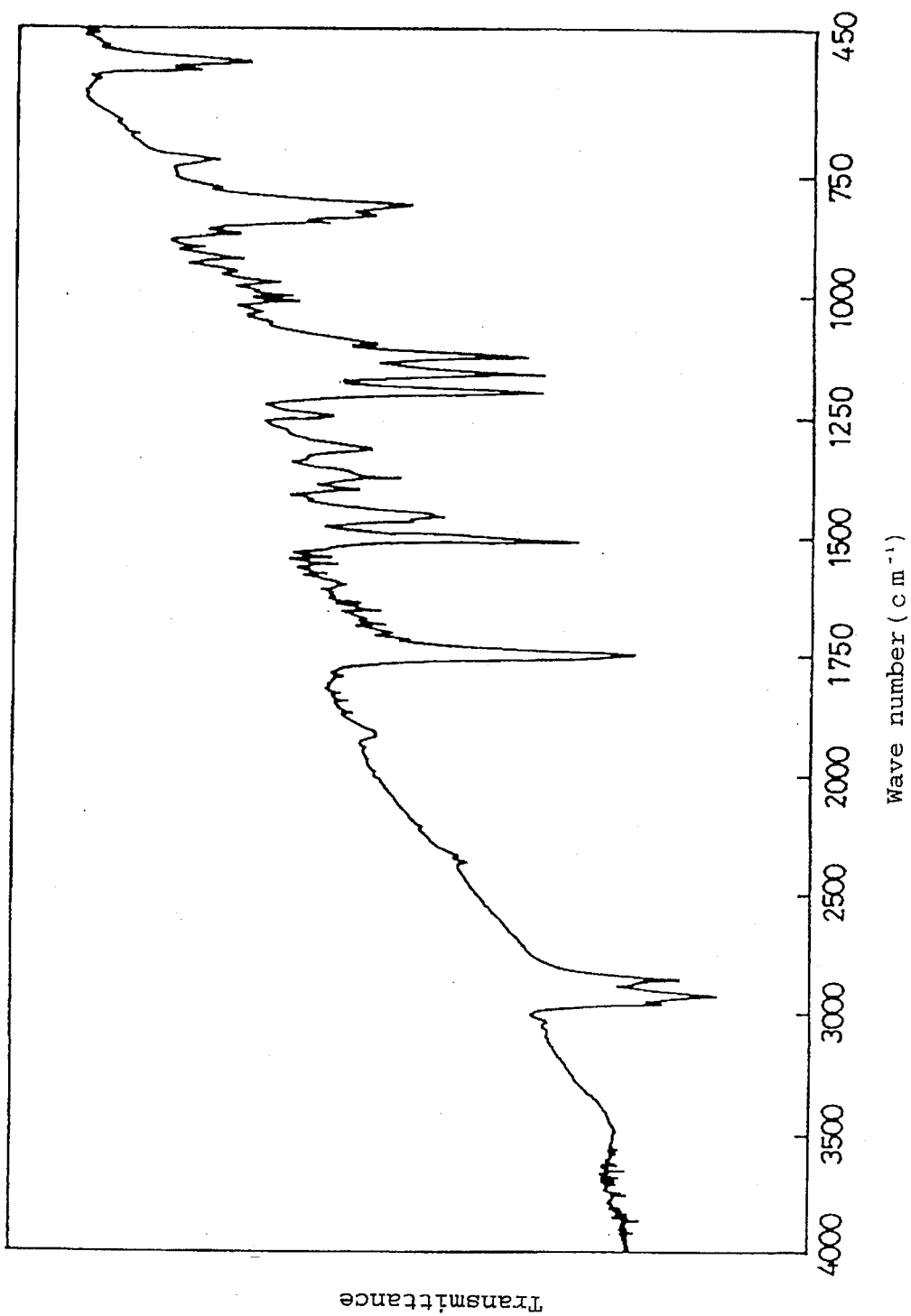
FIG. 17 is a diagram showing an infrared absorption spectrum of the tolan compound prepared in Example 30.

This compound had a nematic liquid crystal phase, a C-N point of 207° C., and an N-I point of 302° C. The IR spectrum of this compound is shown in FIG. 17.

Example 31

A liquid crystal composition was prepared by blending 95 parts by weight of a commercially available nematic liquid crystal composition, ZLI-1132™ (a product of Merck), and 5 parts by weight of the tolan compound of the present invention prepared in Example 27. The properties of the liquid crystal composition are shown in Table 3.

The properties of the liquid crystal composition, ZLI-1132™, were as follows:

NI point: 72° C.
Δn: 0.138
Viscosity: 27.9 cp
Vth: 1.83 V

Examples 32–34

Liquid crystal compositions were prepared in the same manner as in Example 31 from 95 parts by weight of the liquid crystal composition ZLI-1132™ and 5 parts by weight of the tolan compounds of the present invention prepared in Examples 28–30. The properties of these liquid crystal compositions and the chemical formulas of the tolan compounds of the present invention used for these compositions are given in Table 3, which includes the corresponding data for the liquid Crystal composition of Example 31 and the properties of the liquid crystal composition ZLI-1132™.

As can be seen from Table 3, when added in a small amount the tolan compounds of the present invention remarkably increase the N-I point and double refractive index (Δn) of the liquid crystal compounds which contain these compounds.

TABLE 3

| Example No. | Chemical Formula | N-I Point (°C.) | Δn at 25° C. | Viscosity (cP) at 20° C. | Vth (V) at 25° C. |
| --- | --- | --- | --- | --- | --- |
| 31 | C$_4$H$_9$—⟨H⟩—COO—⟨O⟩—⟨O⟩—C≡C—⟨O⟩—C$_2$H$_5$ | 81.0 | 0.146 | 30.3 | 1.86 |
| 32 | C$_4$H$_9$—⟨H⟩—COO—⟨O⟩—⟨O⟩—C≡C—⟨O⟩—C$_3$H$_7$ | 80.9 | 0.146 | 29.4 | 1.87 |

TABLE 3-continued

| Example No. | Chemical Formula | N-I Point (°C.) | Δn at 25° C. | Viscosity (cP) at 20° C. | Vth (V) at 25° C. |
|---|---|---|---|---|---|
| 33 | 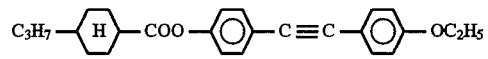 | 80.4 | 0.146 | 29.7 | 1.85 |
| 34 | 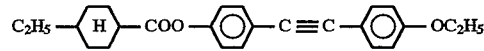 | 80.3 | 0.146 | 30.3 | 1.89 |
| ZLI-1132 | | 72.0 | 0.138 | 27.9 | 1.83 |

Example 35

26 g of 4-bromophenol, 100 ml of dimethylformamide, and 13 g of pyridine were dissolved. 31 g of commercially available trans-4-n-butylcyclohexane carboxylic acid chloride was added dropwise to the solution and the mixture was heated while stirring. The reaction mixture was poured into water to produce crystals. The crystals were collected by filtration, washed with dilute HCl and then water, dried in vacuum, and recrystallized from a mixed solvent of ethyl acetate and methanol to obtain 44 g of 4-bromophenyl trans-4-n-butylcyclohexane carboxylate. To this were added 20 g of 4-ethoxyphenyl acetylene, 0.09 g of bis(triphenylphosphine)-palladium(II) chloride, 0.1 g of copper iodide, 0.79 g of triphenylphosphine, and 260 ml of triethylamine, and the mixture was heated while stirring. After the reaction, the reaction product was poured into water and neutralized with HCl to produce crystals. The crystals were collected by filtration, washed with water, dried in vacuum, and recrystallized from a mixed solvent of ethyl acetate and methanol to obtain 40 g of a compound having the following formula.

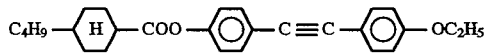

Figure 18:
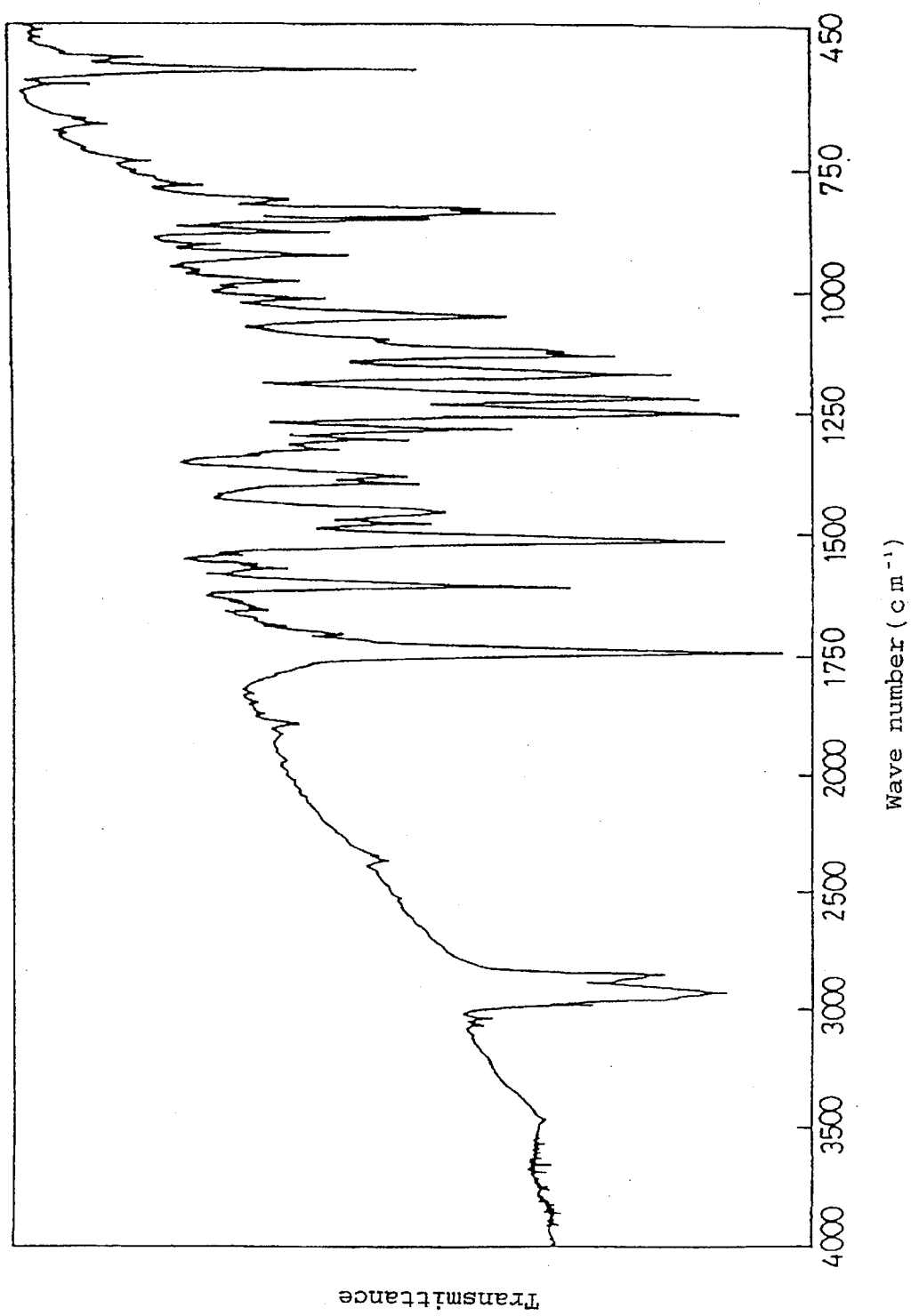
FIG. 18 is a diagram showing an infrared absorption spectrum of the tolan compound prepared in Example 35.

This compound had a nematic liquid crystal phase, a C-N point (crystal-nematic phase transfer temperature) of 99° C., and an N-I point of 252° C. The IR spectrum of this compound is shown in FIG. 18.

Example 36

36 g of a compound having the following formula was prepared in the same manner as in Example 35, except for using 29 g of trans-4-propylcyclohexane carboxylic acid chloride instead of 31 g of trans-4-n-butylcyclohexane carboxylic acid chloride and further using 16 g of 4-fluorophenyl acetylene instead of 20 g of 4-ethoxyphenyl acetylene.

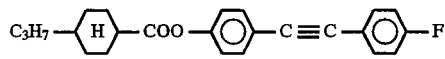

Figure 19:
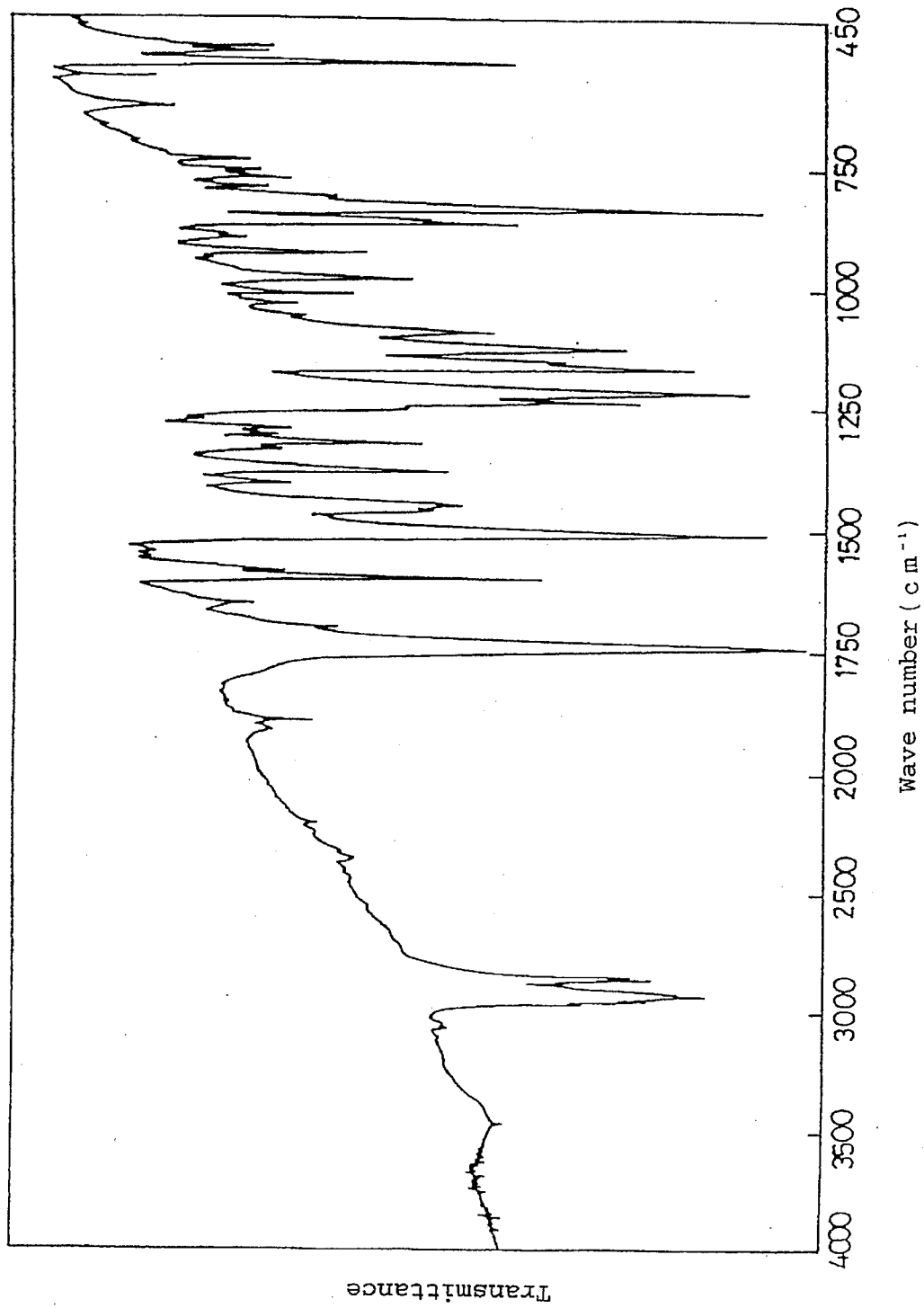
FIG. 19 is a diagram showing an infrared absorption spectrum of the tolan compound prepared in Example 36.

This compound had a nematic liquid crystal phase, a C-N point of 119° C., and an N-I point of 209° C. The IR spectrum of this compound is shown in FIG. 19.

Example 37

38 g of a compound having the following formula was prepared in the same manner as in Example 35, except for using 29 g of trans-4-n-propylcyclohexane carboxylic acid chloride instead of 31 g of trans-4-n-butylcyclohexane carboxylic acid chloride.

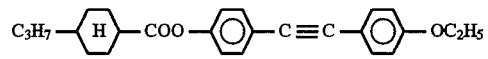

Figure 20:
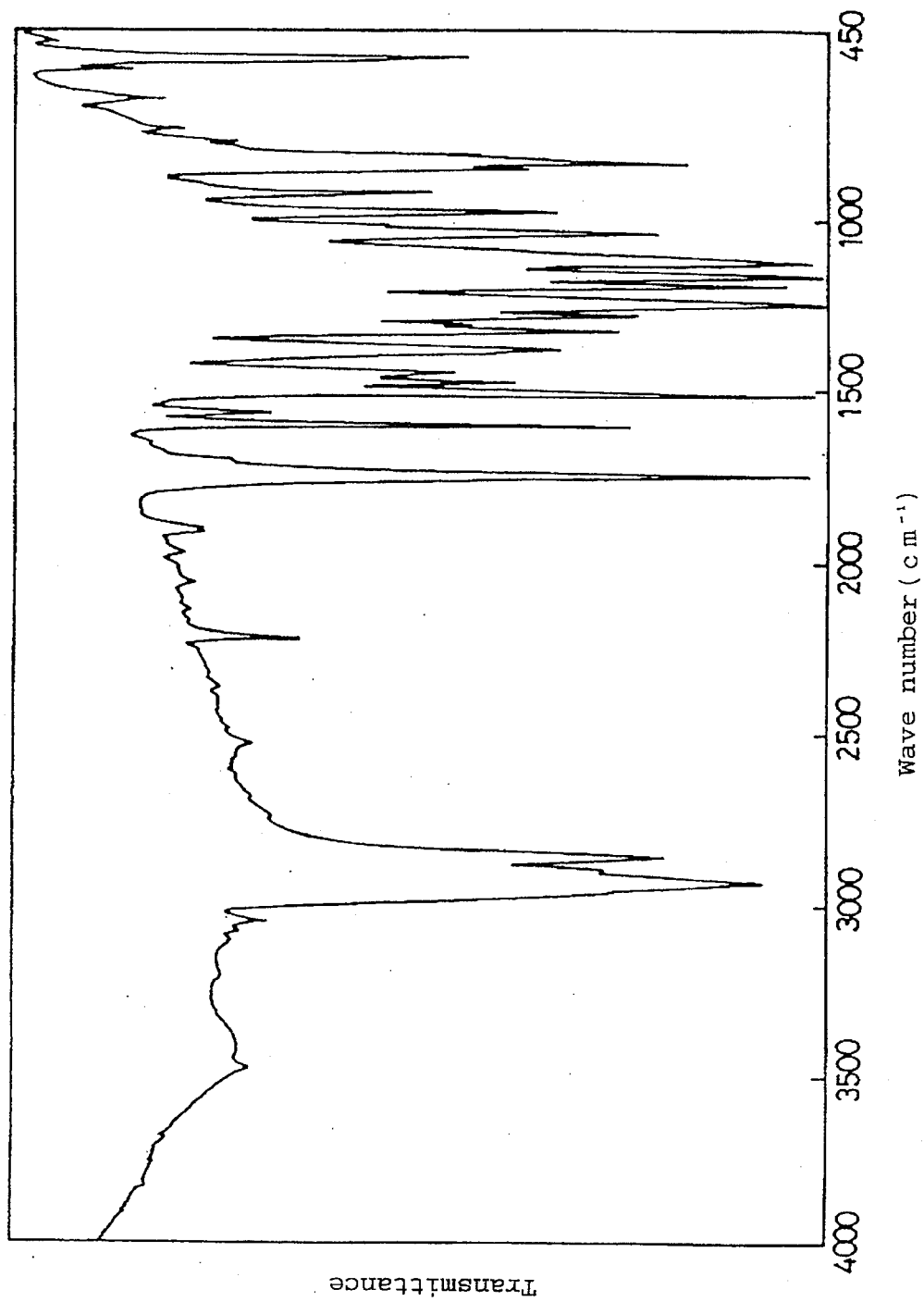
FIG. 20 is a diagram showing an infrared absorption spectrum of the tolan compound prepared in Example 37.

This compound had a nematic liquid crystal phase, a C-N point of 107° C., and an N-I point of 260° C. The IR spectrum of this compound is shown in FIG. 20.

Example 38

37 g of a compound having the following formula was prepared in the same manner as in Example 35, except for using 28 g of trans-4-n-ethylcyclohexane carboxylic acid chloride instead of 31 g of trans-4-n-butylcyclohexane carboxylic acid chloride.

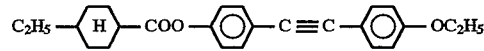

Figure 21:
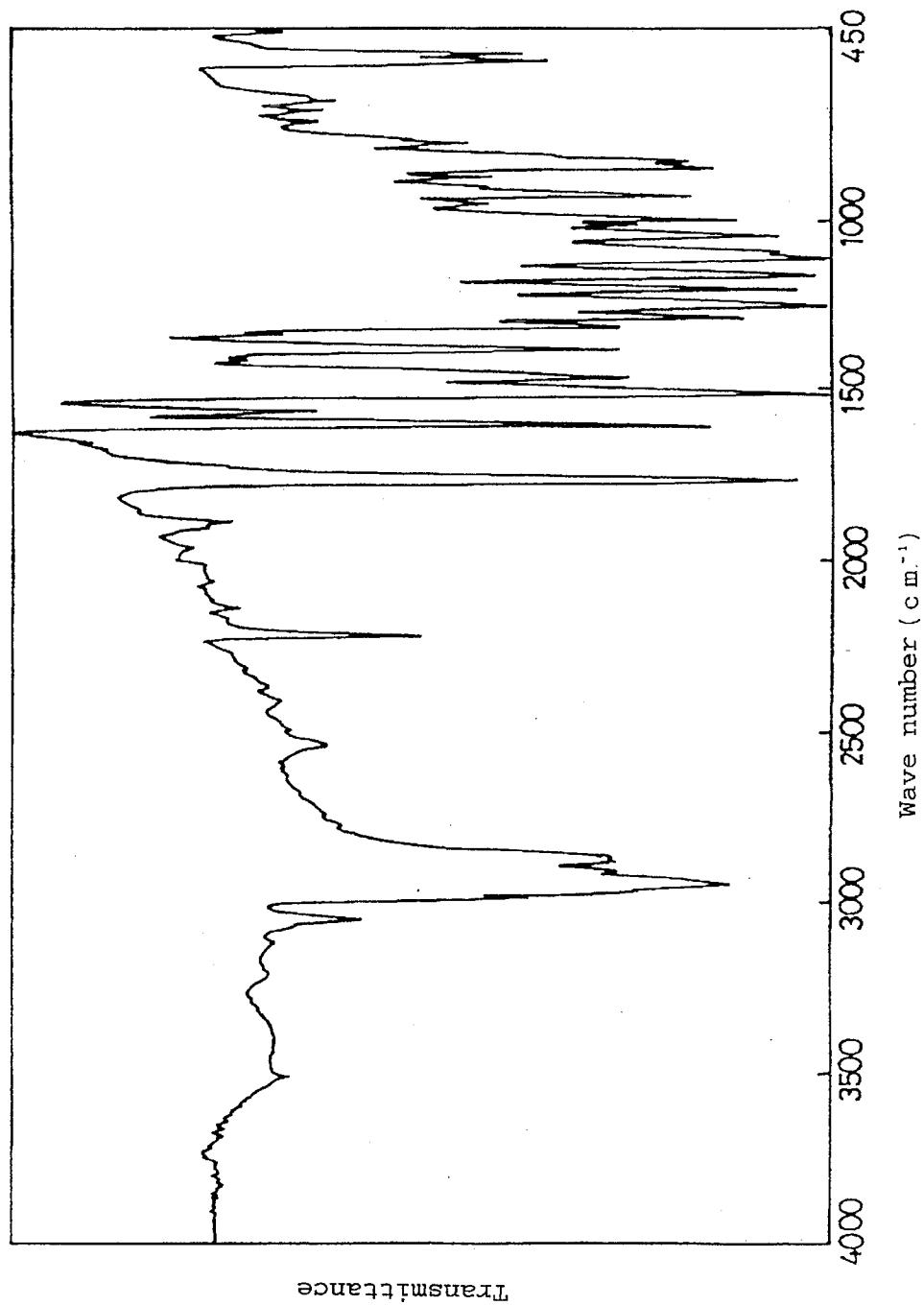
FIG. 21 is a diagram showing an infrared absorption spectrum of the tolan compound prepared in Example 38.

This compound had a nematic liquid crystal phase, a C-N point of 93° C., and an N-I point of 240° C. The IR spectrum of this compound is shown in FIG. 21.

Example 39

40 g of a compound having the following formula was prepared in the same manner as in Example 35, except for using 32 g of trans-4-n-pentylcyclohexane carboxylic acid chloride instead of 31 g of trans-4-n-butylcyclohexane carboxylic acid chloride.

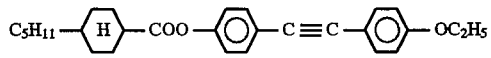

Figure 22:
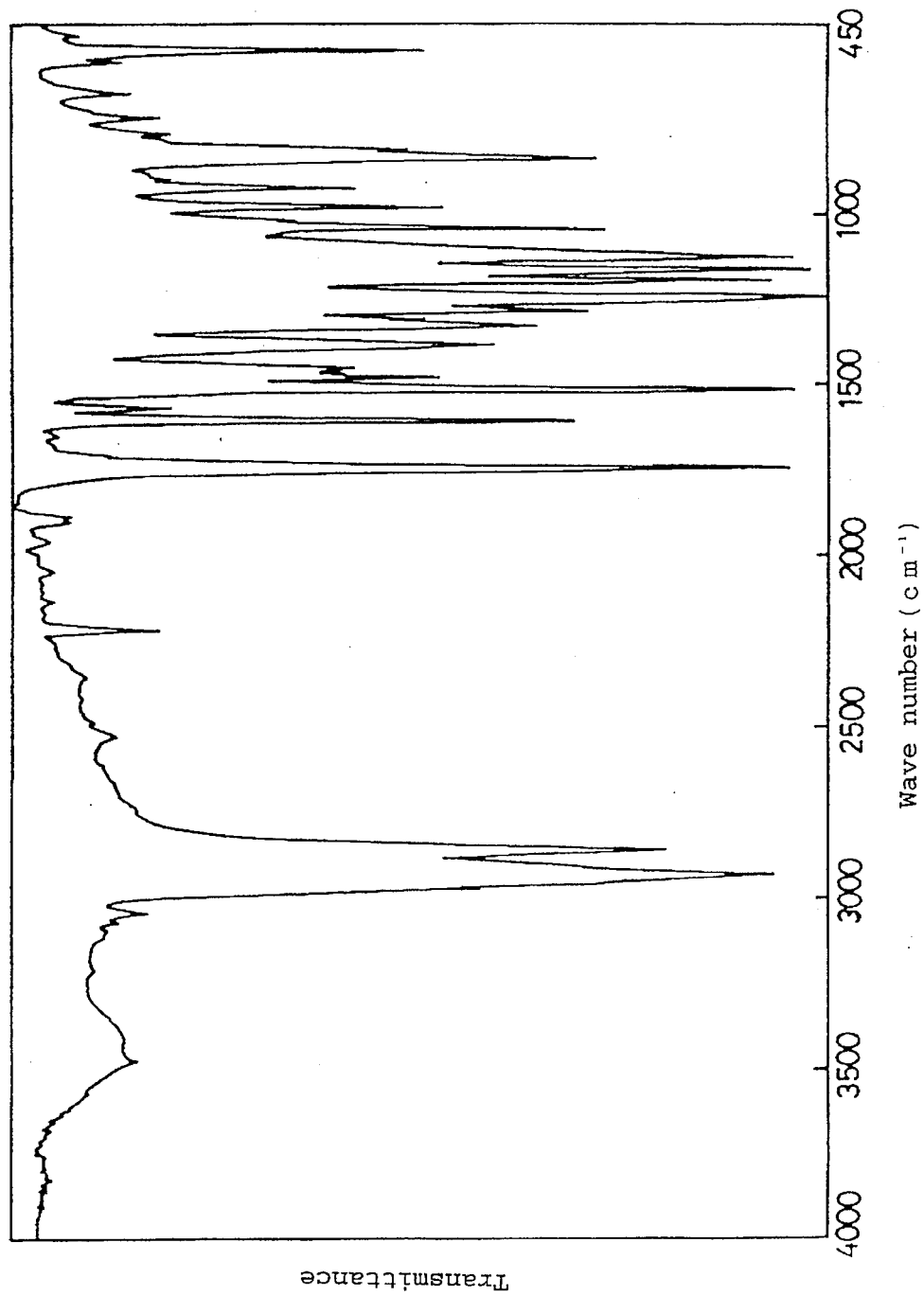
FIG. 22 is a diagram showing an infrared absorption spectrum of the tolan compound prepared in Example 39.

This compound had a nematic liquid crystal phase, a C-N point of 105° C. and an N-I point of 249° C. The IR spectrum of this compound is shown in FIG. 22.

Example 40

41 g of a compound having the following formula was prepared in the same manner as in Example 35, except for using 33 g of trans-4-n-hexylcyclohexane carboxylic acid chloride instead of 31 g of trans-4-n-butylcyclohexane carboxylic acid chloride.

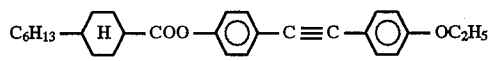

Figure 23:
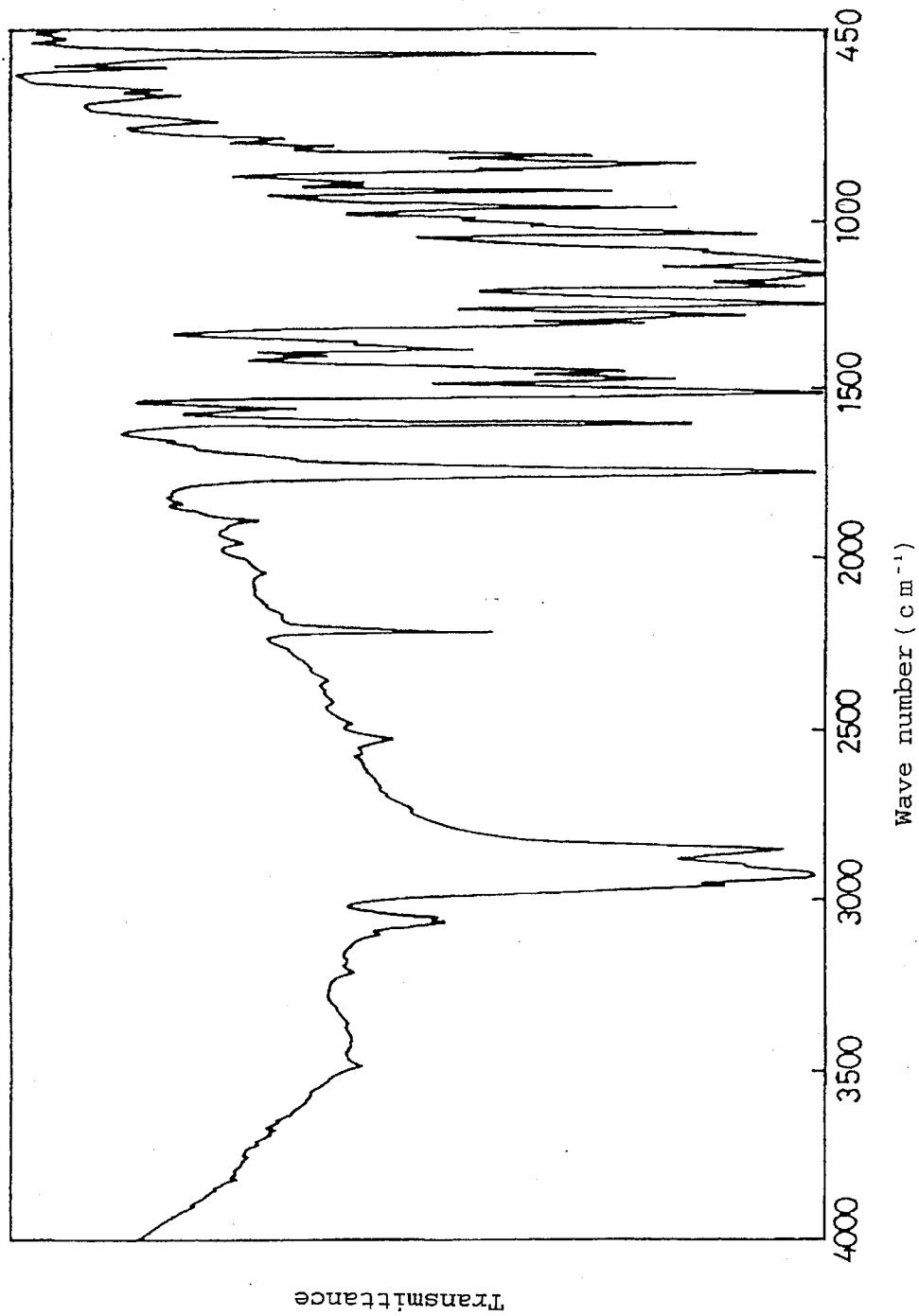
FIG. 23 is a diagram showing an infrared absorption spectrum of the tolan compound prepared in Example 40.

This compound had a nematic liquid crystal phase, a C-N point of 107° C., and an N-I point of 239° C. The IR spectrum of this compound is shown in FIG. 23.

Example 41

A liquid crystal composition was prepared by blending 90 parts by weight of a commercially available nematic liquid crystal composition, ZLI-1132™ (a product of Merck), and 10 parts of the tolan compound of the present invention prepared in Example 35. The properties of the liquid crystal composition are shown in Table 4.

The properties of the liquid crystal composition, ZLI-1132™, were as follows:

NI point: 72° C.
Δn: 0.138
Viscosity: 27.9 cP
Vth: 1.83 V

Examples 42–46

Liquid crystal compositions were prepared in the same manner as in Example 41 from 90parts by weight of the liquid crystal composition, ZLI-1132™ and 10 parts by weight of the tolan compounds of the present invention prepared in Examples 36–40. The properties of these liquid crystal compositions and the chemical formulas of the tolan compounds of the present invention used for these compositions are given in Table 4, which also shows the corresponding data for the liquid crystal composition of Example 41 and the properties of the liquid crystal composition ZLI-1132™.

As can be seen from Table 4, the tolan compounds of the present invention increase the N-I point and double refractive index (Δn) of the liquid crystal compounds which contain these compounds.

The tolan compounds of the present invention can increase the N-I point and double refractive index (Δn) of a liquid crystal composition and, when the compounds have an electron attractive group, such as cyano group or halogen atom, for the terminal group $R_1$, exhibit a decreased threshold voltage Vth. The liquid crystal composition comprising the tolan compound of the present invention, therefore, has excellent characteristics as a liquid crystal material, and the liquid crystal display device using this liquid crystal composition has a wide temperature range and a wide visible angle and can be operated a low driving voltage. In addition, because the tolan compounds of the present invention has sufficient compatibility with various other compounds, they can be used to improve the characteristics of liquid crystal compositions by using in combination with a number of other liquid crystal materials.

Obviously, numerous modifications and variations of the present invention are possible in light of the above teachings. It is therefore to be understood that, within the scope of the appended claims, the invention may be practiced otherwise than as specifically described herein.

What is claimed is:

1. A tolan compound represented by the following formula (Ia):

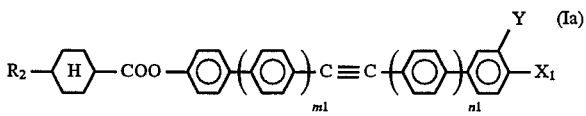

wherein $R_2$ represents a hydrogen atom or an alkyl group having 1–10 carbon atoms; $X_1$ represents a halogen atom, an alkyl group having 1–10 carbon atoms, or an alkoxy group having 1–10 carbon atoms; Y represents a hydrogen atom or a halogen atom; and m1 and n1 are individually an integer of 0 or 1, provided that m1+n1 is 1.

2. A tolan compound represented by the following formula (Ib):

TABLE 4

| Example No. | Chemical Formula | N-I Point (°C.) | Δn at 25° C. | Viscosity (cP) at 20° C. | Vth (V) at 25° C. |
|---|---|---|---|---|---|
| 41 | $C_4H_9$—⟨H⟩—COO—⟨○⟩—C≡C—⟨○⟩—$OC_2H_5$ | 86.6 | 0.149 | 29.5 | 1.90 |
| 42 | $C_3H_7$—⟨H⟩—COO—⟨○⟩—C≡C—⟨○⟩—F | 79.5 | 0.145 | 29.1 | 1.89 |
| 43 | $C_3H_7$—⟨H⟩—COO—⟨○⟩—C≡C—⟨○⟩—$OC_2H_5$ | 87.3 | 0.150 | 30.1 | 1.88 |
| 44 | $C_2H_5$—⟨H⟩—COO—⟨○⟩—C≡C—⟨○⟩—$OC_2H_5$ | 85.8 | 0.149 | 28.9 | 1.82 |
| 45 | $C_5H_{11}$—⟨H⟩—COO—⟨○⟩—C≡C—⟨○⟩—$OC_2H_5$ | 87.7 | 0.148 | 29.0 | 1.85 |
| 46 | $C_6H_{13}$—⟨H⟩—COO—⟨○⟩—C≡C—⟨○⟩—$OC_2H_5$ | 86.5 | 0.147 | 29.7 | 1.84 |
| ZLI-1132 | | 72.0 | 0.138 | 27.9 | 1.83 |

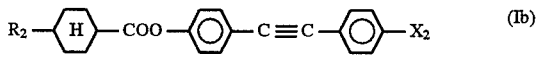

wherein $R_2$ represents a hydrogen atom or an alkyl group having 1–10 carbon atoms and $X_2$ represents a halogen atom, a cyano group, or an alkoxy group having 1–10 carbon atoms.

3. A tolan compound represented by the following formula

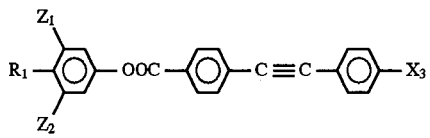 (Ic)

wherein $R_1$ represents a hydrogen atom, a halogen atom, a cyano group, an alkyl group having 1–10 carbon atoms, or an alkoxy group having 1–10 carbon atoms; $X_3$ represents a hydrogen atom or an alkyl group having 1–10 carbon atoms; and $Z_1$ and $Z_2$ represent individually a hydrogen atom or a halogen atom.

4. A liquid crystal composition comprising at least one tolan compound defined in claim 1.

5. A liquid crystal composition comprising at least one tolan compound defined in claim 2.

6. A liquid crystal composition comprising at least one tolan compound defined in claim 3.

7. A liquid crystal display device using the liquid crystal composition defined in claim 4.

8. A liquid crystal display device using the liquid crystal composition defined in claim 5.

9. A liquid crystal display device using the liquid crystal composition defined in claim 6.

\* \* \* \* \*